US008293508B2

(12) United States Patent
Lantero et al.

(10) Patent No.: US 8,293,508 B2
(45) Date of Patent: Oct. 23, 2012

(54) METHODS FOR PRODUCING ETHANOL FROM CARBON SUBSTRATES

(75) Inventors: Oreste Lantero, Belvidere, IL (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 776 days.

(21) Appl. No.: 11/243,382

(22) Filed: Oct. 4, 2005

(65) Prior Publication Data

US 2006/0084156 A1    Apr. 20, 2006

Related U.S. Application Data

(63) Continuation of application No. 10/360,010, filed on Feb. 6, 2003, now abandoned.

(60) Provisional application No. 60/355,180, filed on Feb. 8, 2002.

(51) Int. Cl.
*C12P 7/06* (2006.01)

(52) U.S. Cl. ........ 435/161; 435/162; 435/163; 435/165; 435/171

(58) Field of Classification Search .................. 435/161, 435/163, 165, 171, 202, 205, 223, 225, 256.6, 435/254.3
See application file for complete search history.

(56) References Cited

U.S. PATENT DOCUMENTS

| | | | |
|---|---|---|---|
| 4,092,434 A | 5/1978 | Yoshizumi et al. | |
| 4,316,956 A | 2/1982 | Lützen | 435/96 |
| 4,346,113 A | 8/1982 | Faust et al. | |
| 4,460,687 A | 7/1984 | Ehnström | 435/161 |
| 4,514,496 A | 4/1985 | Yoshizumi et al. | |
| 4,618,579 A | 10/1986 | Dwiggins et al. | |
| 4,727,026 A | 2/1988 | Sawada et al. | 435/96 |
| 5,000,000 A | 3/1991 | Ingram et al. | |
| 5,008,473 A | 4/1991 | Breitkopf et al. | |
| 5,028,539 A | 7/1991 | Ingram et al. | |
| 5,231,017 A | 7/1993 | Lantero et al. | |
| 5,356,812 A | 10/1994 | Matsuyama et al. | |
| 5,424,202 A | 6/1995 | Ingram et al. | |
| 5,482,846 A | 1/1996 | Ingram et al. | |
| 5,487,989 A | 1/1996 | Fowler et al. | |
| 5,514,583 A | 5/1996 | Picataggio et al. | |
| 5,554,520 A | 9/1996 | Fowler et al. | |
| 5,599,689 A | 2/1997 | Haynie et al. | |

FOREIGN PATENT DOCUMENTS

| | | |
|---|---|---|
| DE | 35 41 129 A1 | 6/1986 |
| EP | 0 171 218 B1 | 10/1993 |
| WO | WO 95/13362 | 5/1995 |

OTHER PUBLICATIONS

Garg, SK et al. Optimization of cassava starch conversion to glucose by *Rhizopus oligosporus*. MIRCEN Journal. 1989. 5: 297-305.*

Brown, S. W. and Oliver, S. G., "The Effect of Temperature on the Ethanol Tolerance of the Yeast," *Biotechnology Letters*, 4:269-274 (1982).
Casey, G. P. and Ingledew, W. M., "Reevaluation of Alcohol Synthesis and Tolerance in Brewer's Yeast," *Journal of the American Society of Brewing Chemists*, Inc. 43(2):75-83 (1985).
Han, I et al., "Amylolysis of Raw Corn by *Aspergillus Niger* for Simultaneous Ethanol Fermentation," *Biotechnology and Bioengineering*, 30:225-233 (1987).
Hayashida, S., Selective Submerged Productions of Three Types of Glucoamylases by a Black-koji Mold., *Agr. Biol. Chem.*, 39:11, 2093-2099 (1975).
Jones, A. M. and Ingledew, W. M., "Fuel Alcohol Production: Optimization of Temperature for Efficient Very-High-Gravity Fermentation," *Appl. Environ. Microbiol.*, 60(3):1048-1051 (1994).
Lewis, S. M., "Fermentation Alcohol". Chapter 2.1 in *Industrial Enzymology* ($2^{nd}$ Ed. 1996).
Matsumoto, N. et al., "Industrialization of a Noncooking System for Alcoholic Fermentation from Grains," *Agric. Biol. Chem.*, 46(6):1549-1558 (1982).
Matsuoka, H. et al., "Alcoholic Fermentation of Sweet Potato without Cooking," *Journal of Fermentation Technology*, 60(6):599-602 (1982).
Medda, S. et al., "Glucoamylase I of Black *Aspergillus*," *J. Fac. Agr., Kyushu Univ.*, 26 (2.3), 139-149 (1982).
Sa-Correia, I. and Van Uden, N., "Effects of Ethanol on Thermal Death and on the Maximum Temperature for Growth of the Yeast *Kluyveromyces fragilis*," *Biotechnol. Lett.*, 4(12):805-808 (1982).
Ueda, S. et al., "Direct Hydrolysis of Raw Starch," *Microbiological Sciences*, 1(1):21-24 (1984).
Van Uden, N. and da Cruz Duarte, H., Effects of Ethanol on the Temperature Profile of *Saccharomyces cerevisiae, Zeitsch. Allg. Mikrobiol.*, 21(10):743-750 (1981).
Van Uden, N. et al., "Effects of Ethanol on Yeast Performance: Targets and Underlying Mechanisms," *Proceedings of the 19th Congress of European Brewery Convention*, pp. 137-144 (1983).
Bowien, B. et al., "Genetic Regulation of CO2 Assimilation in Chemoautotrophs," *Microbial Growth on C1 Compounds*, pp. 481-491, Intercept LTD., PO Box 716, Andover, Hampshire S10 1 YG, UK (1993).
Hayashida, S., "Selective Submerged Productions of Three Types of Glucoamylases by a Black-koji Mold," *Agr. Biol. Chem.*, 39(11):2093-2099 (1975).
Hunter, B. et al., "Formaldehyde Metabolism by *Escherichia coli*. Carbon and Solvent Deuterium Incorporation into Glycerol, 1,2-Propanediol, and 1,3-Propanediol," *Biochemistry*, 24:4148-4155 (1985).
Nakamura, L. K., "*Lactobacillus amylovorus*, a New Starch-Hydrolyzing Species from Cattle Waste-Corn Fermentations," *International Journal of Systematic Bacteriology*, 31(1):56-63 (1981).
Xiaodong, W. et al., "Direct Fermentative Production of Lactic Acid on Cassava and Other Starch Substrates," *Biotechnology Letters*, 19(9):841-843 (1997).

(Continued)

*Primary Examiner* — Allison Ford
*Assistant Examiner* — Susan E Fernandez
(74) *Attorney, Agent, or Firm* — Danisco US Inc.

(57) ABSTRACT

The present invention provides means for the production of desired end-products of in vitro and/or in vivo bioconversion of biomass-based feed stock substrates, including but not limited to such materials as starch and cellulose. In particularly preferred embodiments, the methods of the present invention do not require gelatinization and/or liquefaction of the substrate. In particularly preferred embodiments, the present invention provides means for the production of ethanol.

12 Claims, 7 Drawing Sheets

OTHER PUBLICATIONS

International Search Report for PCT/US03/03670 filed Feb. 6, 2003.

Arfman, N. et al., "Use of the *tac* Promoter and lac*I*$^q$ for the Controlled Expression of *Zymomonas mobilis* Fermentative Genes in *Escherichia coli* and *Zymomonas mobilis*," Journal of Bacteriology, vol. 174, No. 22, pp. 7370-7378, Nov. 1992.

Bowien et al., "CO2 Assimilation in Chemoautotrophs, *Microbial Growth on C1 Compounds*," 484-485—Book (not sent).

Conway, T. et al., "Promoter and Nucleotide Sequences of the *Zymomonas mobilis* Pyruvate Decarboxylase," Journal of Bacteriology, vol. 169, No. 3, pp. 949-954, Mar. 1987.

Hayashida, S., "Selective Submerged Productions of Three Types of Glucoamylases by a Black-koji Mold," *Kyushu University, Fukuoka, Japan*, 2093-2099, (1975).

Hunter et al., "Formaldehyde Metabolism by *Escherichia coli*. Carbon and Solvent Deuterium Incorporation into Glycerol, 1, 2-Propanediol, and 1, 3-Propanediol," *Biochemistry*, 4148-4155, (1985).

Ingram et al., "Genetic Engineering of Ethanol Production in *Escherichia coli*, Applied and Environmental Microbiology, vol. 53, No. 10, pp. 2420-2425," Oct. 1987.

Nakamura, L. K., "*Lactobacillus amylovorus*, a New Starch-Hydrolyzing Species from Cattle Waste-Corn Fermentations," *Intl. J. of Systematic Bacteriology*, 56-63, (1981).

Ohta, Kazuyoshi et al., "Genetic Improvement of *Escherichia coli* for Ethanol Production: Chromosomal Integration of *Zymomonas mobilis* Genes Encoding Pyruvate Decarboxylase and Alcohol Dehydrogenase II," Applied and Environmental Microbiology, vol. 57, No. 4, pp. 893-900, Apr. 1991.

Ohta, Kazuyoshi et al., "Metabolic Engineering of *Klebsiella oxytoca* M5A1 for Ethanol Production from Xylose and Glucose, " Applied and Environmental Microbiology, vol. 57, No. 10, pp. 2810-2815, Oct. 1991.

Saha et al., "Alcoholic Fermentation of Raw Sweet Potato by a Nonconventional Method Using Endomycopsis fibuligera Glycoamylase Preparation," *Biotechnology and Bioengeneering*, vol. XXV, 1181-1186, (1983).

Sandstedt et al., "A standarized Wohlgemuth Procedure for Alpha-Amylase Activity," *Cereal Chemistry*, 712-723, (1939).

Takahashi et al., "Different Behavior towards Raw Starch of Three Forms of Glucoamylase from a *Rhizopus* Sp.,"*J. Biochem.*, 663-671, (1985).

Ueda et al., "Alcoholic Fermentation of Raw Starch without Cooking by using Black-koji Amylase," *J Ferment Technol.*, vol. 58, No. 3, 237-242, (1980).

Ueda et al., "Production of Ethanol from Raw Cassava Starch by a Nonconventional Fermentation Method," *Biotechnology and Bioengineering*, vol. XXIII, 291-299, (1981).

Xiaodong et al., "Direct Fermentative Production of Lactic Acid on Cassava and Other Starch Substrates," *Biotechnology Letters*, vol. 19, No. 9, 841-843, (1997).

Yamada, et al., "Production of Glycerol from Methanol by a Mutant Strain of Candida Boidinni," *Agric. Biol. Chem.*, 541-543, (1989).

Yamamoto et al., "Alpha-Amylase of Rhizopus niveus: Its Isolation and Some Enzyme Properties," *Denpun kagaku*, vol. 37, No. 3, 129-136, (1990).

\* cited by examiner

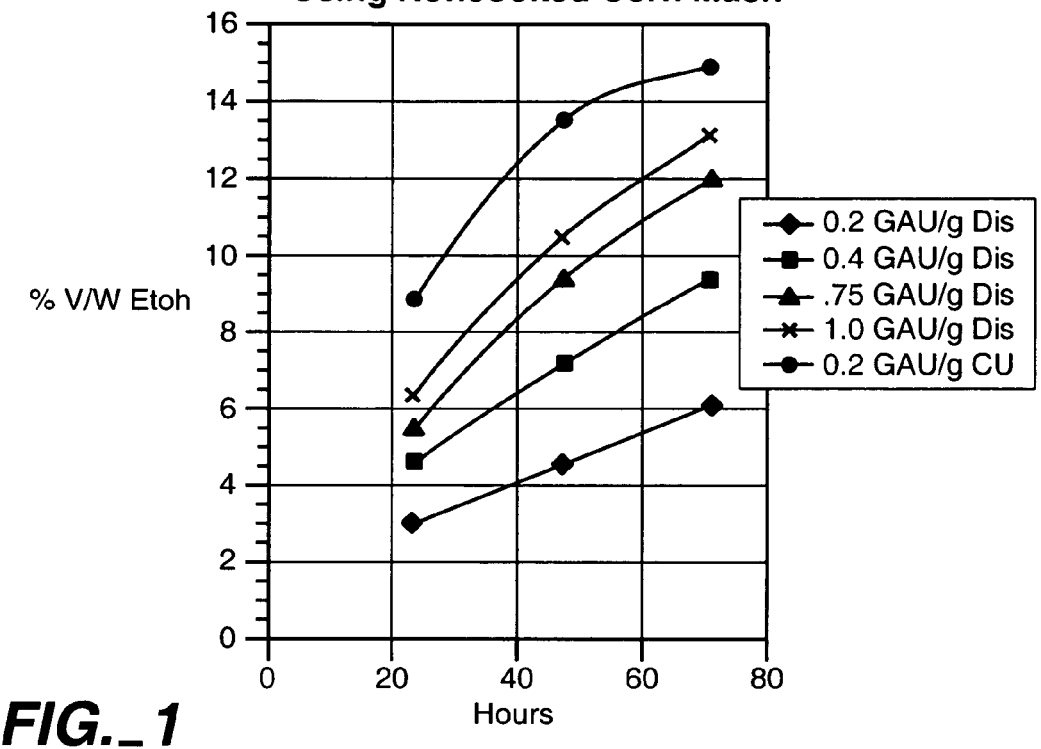
FIG._1
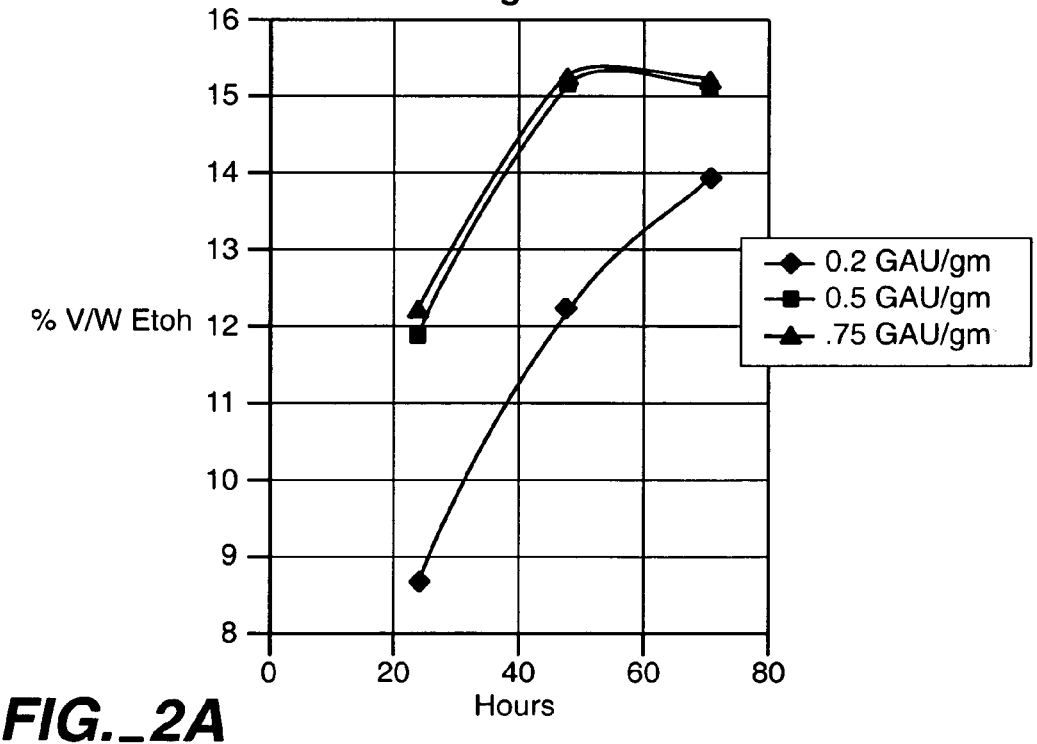
FIG._2A

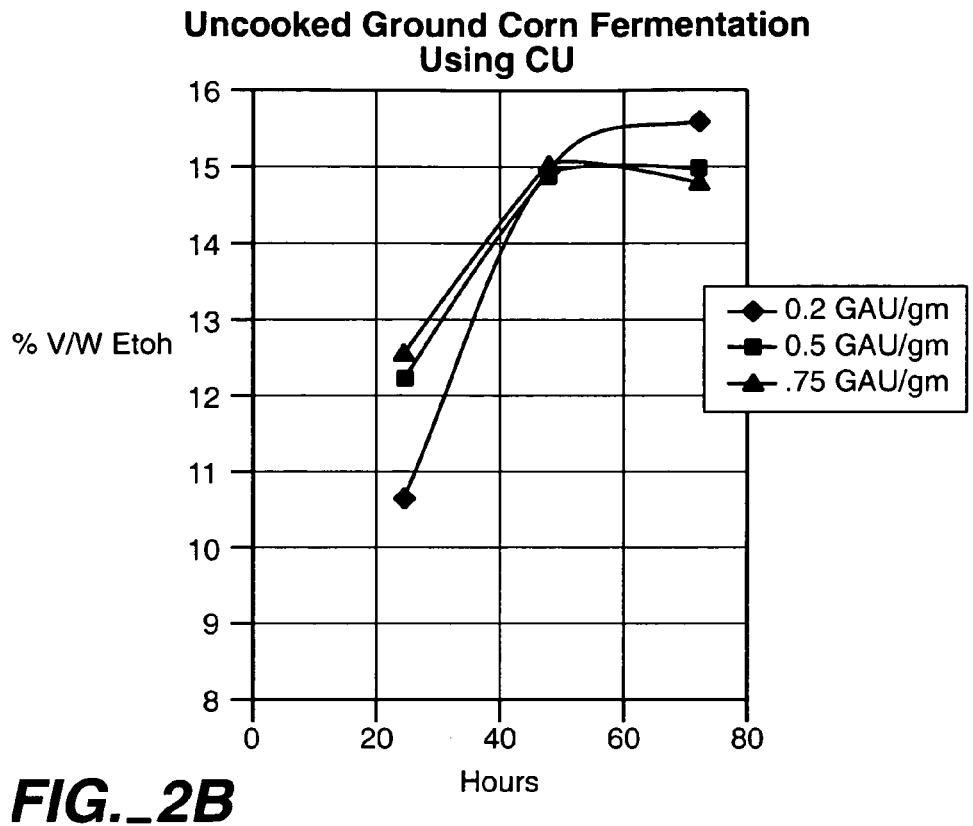
FIG._2B
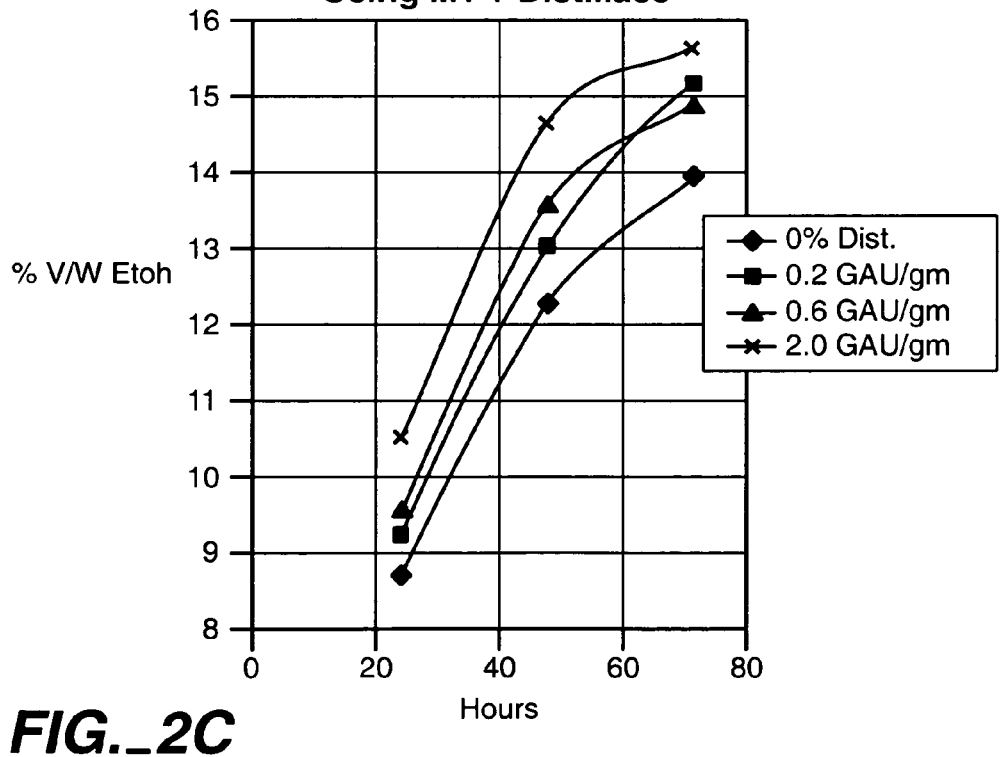
FIG._2C

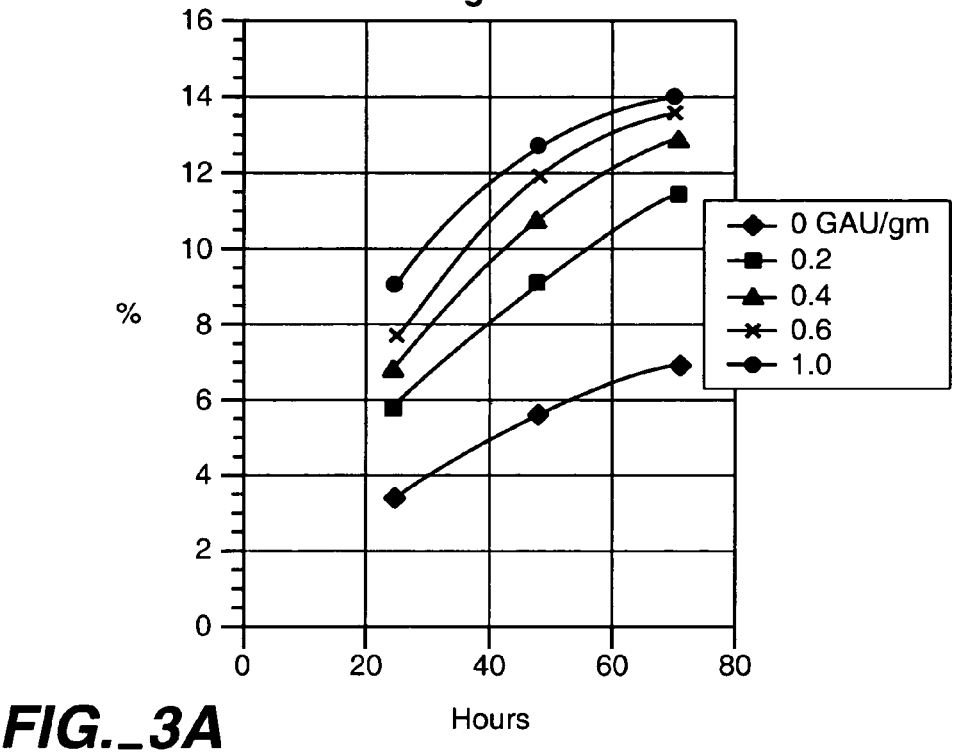
FIG._3A
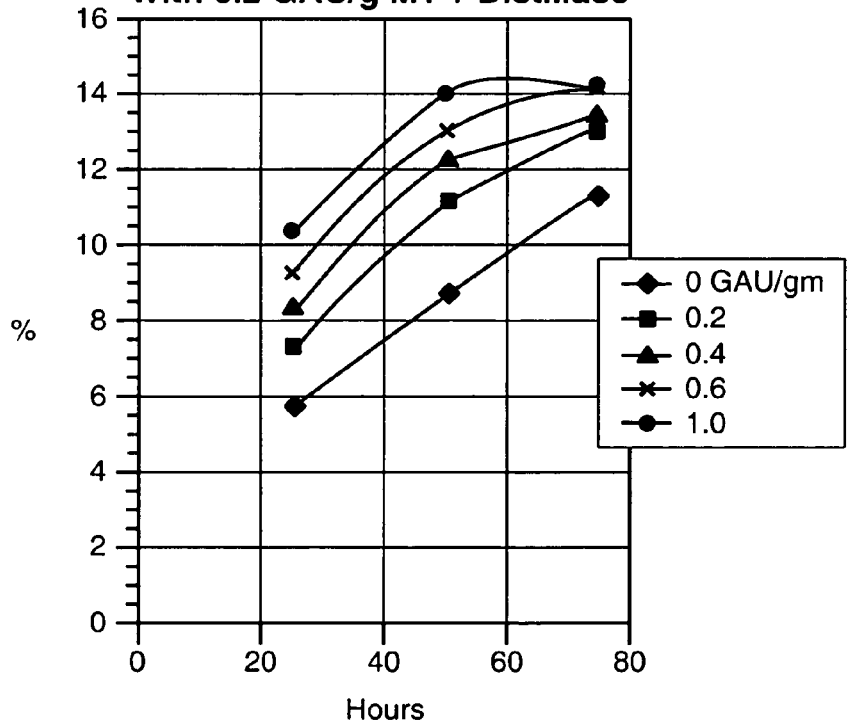
FIG._3B

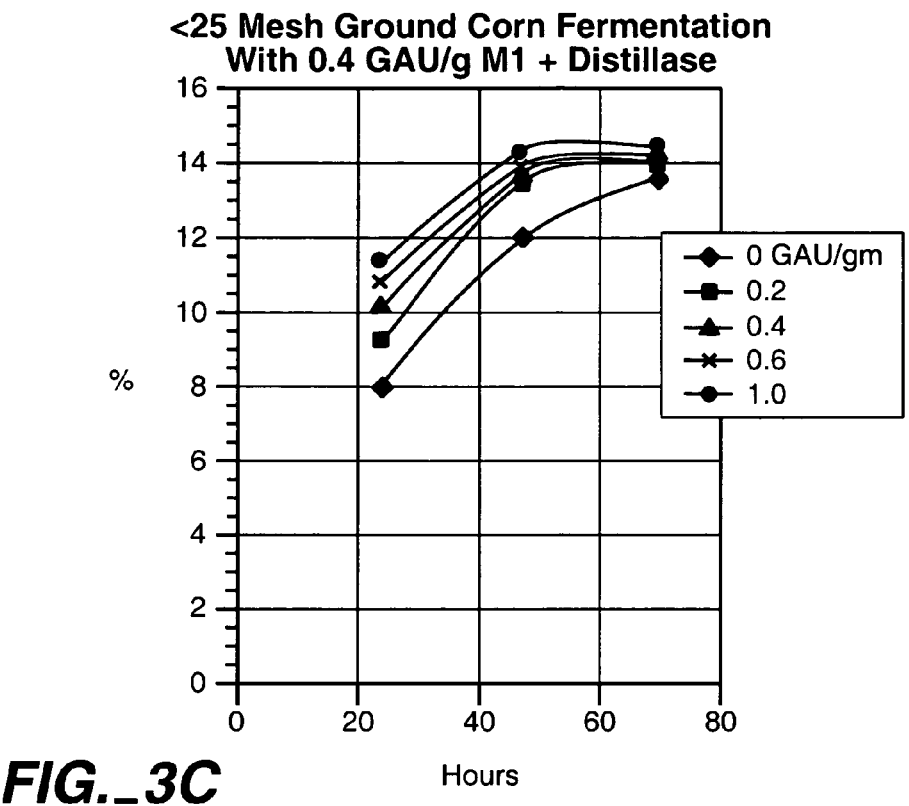
FIG._3C
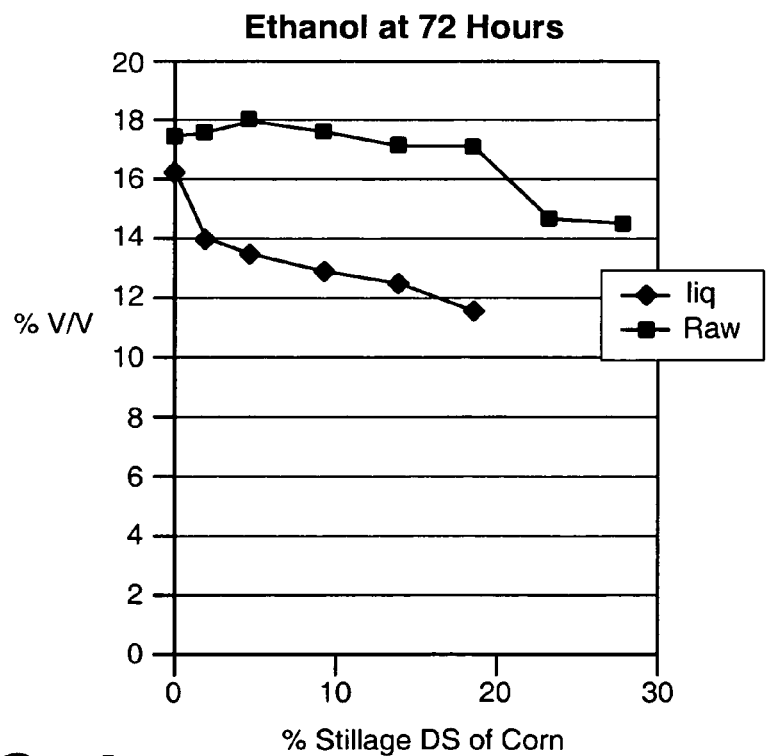
FIG._4

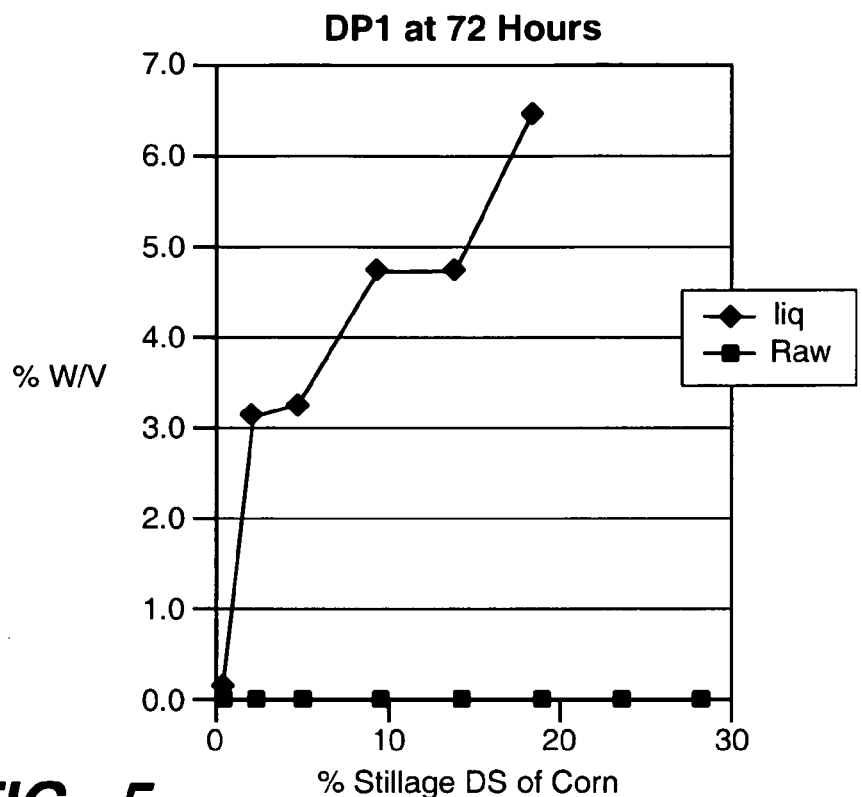
FIG._5
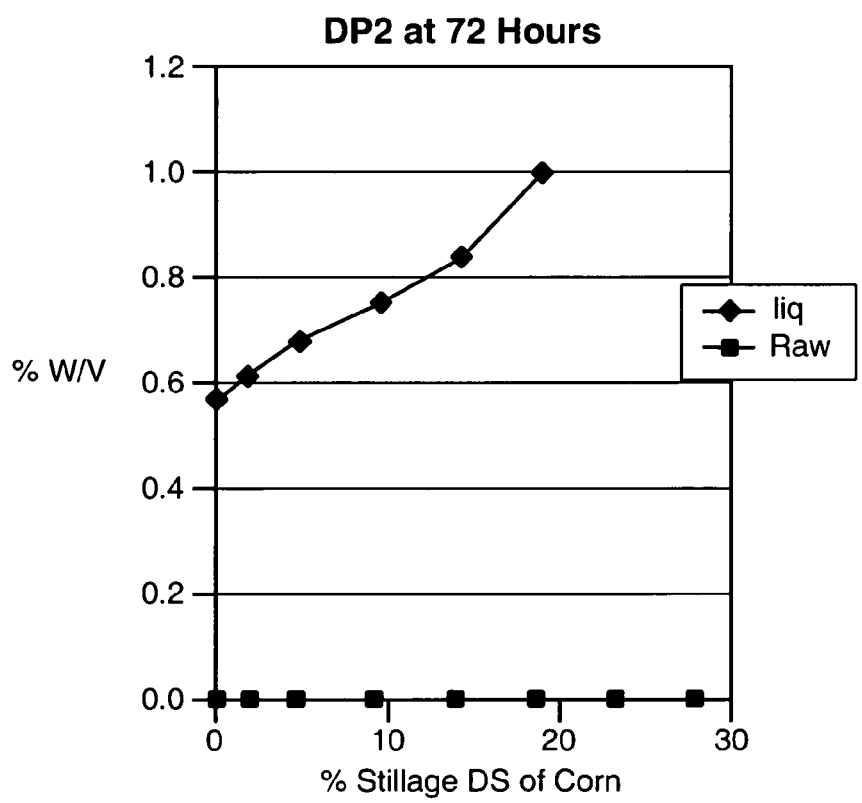
FIG._6

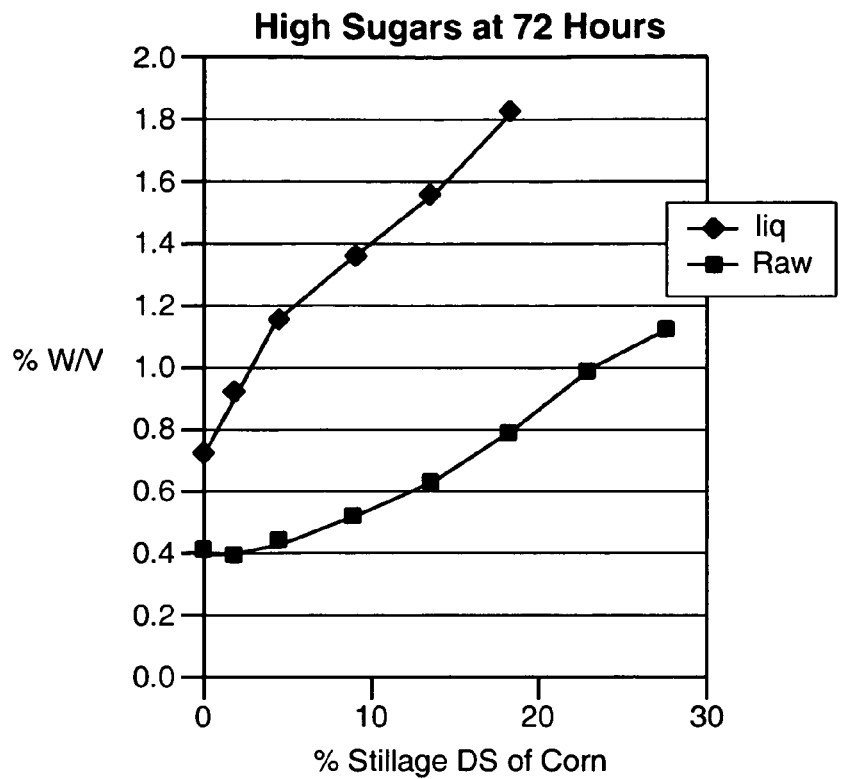
FIG._7
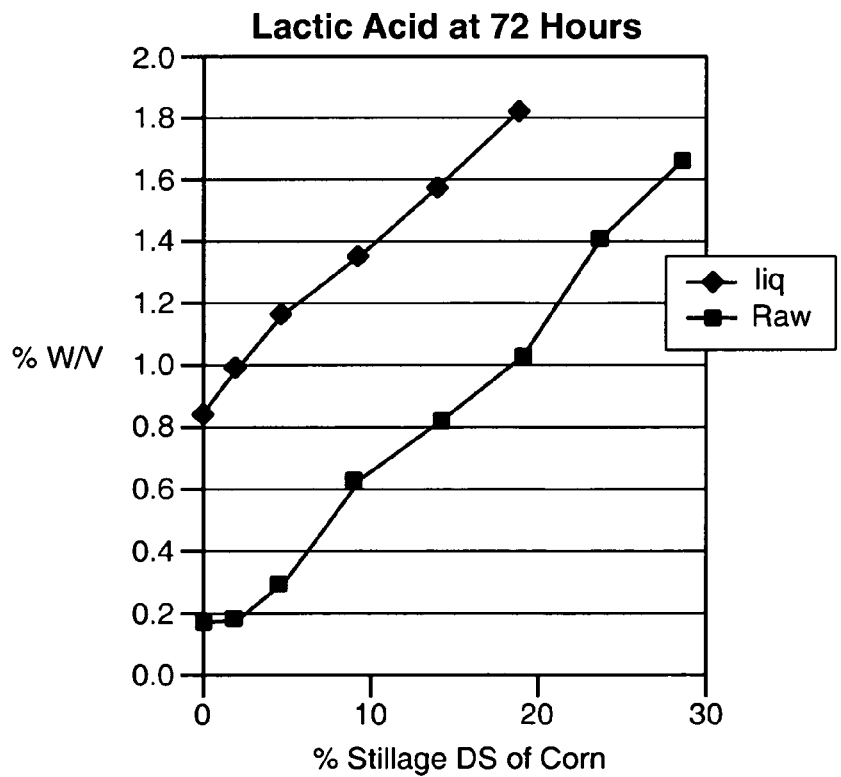
FIG._8

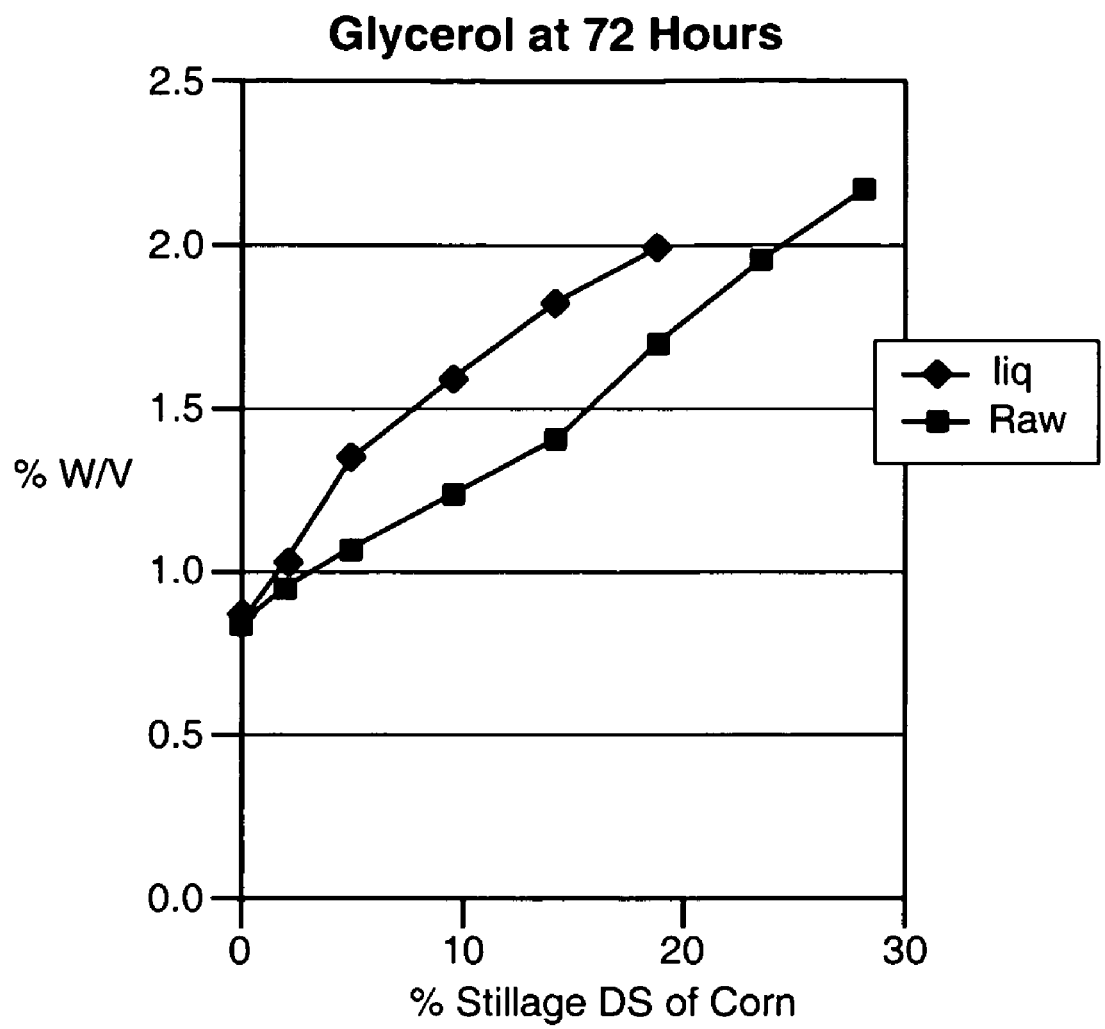
FIG._9

METHODS FOR PRODUCING ETHANOL FROM CARBON SUBSTRATES

This is a continuation of application Ser. No. 10/360,010, filed Feb. 6, 2003 now abandoned, which claims priority to Ser. No. 60/355,180, filed Feb. 8, 2002.

FIELD OF INVENTION

The present invention provides means for the production of desired end-products of in vitro and/or in vivo bioconversion of biomass-based feed stock substrates, including but not limited to such materials as starch and cellulose. In particularly preferred embodiments, the methods of the present invention do not require gelatinization and/or liquefaction of the substrate. In particularly preferred embodiments, the present invention provides means for the production of ethanol.

Background of the Invention

Industrial fermentations predominantly utilize glucose as feed-stock for the production of proteins, enzymes and chemicals. These fermentations are usually batch, fed-batch, or continuous, and operate under conditions that are substrate-limited and/or designed to produce minimal by-products. As those in the art know, there are certain critical operating conditions that must be controlled during fermentation so as to optimize fermentation time, yield and efficiency.

Glucose is a natural, carbon based compound that is useful in a multitude of chemical and biological synthetic applications as a starting substrate. However, syrups that contain glucose purity levels of greater than 90% are relatively expensive. In addition, the presence of high glucose concentrations increases the susceptibility of the fermentation system to microbial contamination, thereby resulting in an adverse effect upon the production efficiency. Another disadvantage is that even the presence of low to moderate levels of glucose in the fermentation vat adversely affects the conversion of the glucose to the desired end product, for example by enzymatic inhibition and/or catabolite repression, and/or the growth of microorganisms. As a result, various attempts have been made to reduce the costs of industrial fermentation, particularly in utilization of substrates that are less expensive than glucose. However, despite the development of numerous approaches, there remains a need in the art for economical, efficiently-utilized substrates for fermentation. Indeed, there is a great need in the art for methods that utilize a less expensive starting material than glucose to more efficiently produce a desired end-product.

SUMMARY OF THE INVENTION

The present invention provides means for the production of desired end-products of in vitro and/or in vivo bioconversion of biomass-based feed stock substrates, including but not limited to such materials as starch and cellulose. In particularly preferred embodiments, the methods of the present invention do not require gelatinization and/or liquefaction of the substrate. In particularly preferred embodiments, the present invention provides means for the production of ethanol. In some particularly preferred embodiments, the present invention provides means for the production of ethanol directly from granular starch, in which altered catabolite repression is involved.

In some embodiments, the present invention provides methods for producing ethanol in which the glucose concentration of the conversion medium is maintained at a low concentration, preferably below the threshold triggering catabolite repression and/or enzyme inhibition, so as to increase efficiency of the process by avoiding catabolic repressive and/or enzymatic inhibitive effects of glucose upon the enzymatic conversion of starch to ethanol.

In additional embodiments, the present invention provides methods for producing ethanol comprising the steps of contacting at least one carbon substrate with at least one substrate converting enzyme, to produce at least one intermediate, and then contacting at least one intermediate with at least one intermediate producing enzyme in a reactor vessel, wherein the at least one intermediate is substantially all bioconverted an end-product. In some preferred embodiments, a microorganism is used to achieve this bioconversion. By maintaining a low concentration of the intermediate in a conversion medium, the intermediate's catabolite repressive and/or enzymatic inhibitive effects are altered (e.g., reduced). The present invention also provides various levels of intermediate concentration, substrates, intermediates and steps of converting the intermediate to ethanol.

The present invention provides methods for producing an alcohol as an end-product comprising the steps of: contacting a carbon substrate and at least one substrate-converting enzyme to produce an intermediate; and contacting the intermediate with at least one intermediate-converting enzyme, wherein the intermediate is substantially all converted by the intermediate enzyme to alcohol. In some preferred embodiments, the intermediate-converting enzyme is a microbial enzyme. In alternative preferred embodiments, the intermediate-converting microbial enzyme is secreted by a microorganism that is in contact with the intermediate. In further embodiments, substrate-converting enzyme is a microbial enzyme. In some preferred embodiments, the substrate-converting microbial enzyme is secreted by a microorganism that is in contact with the substrate. In still other preferred embodiments, the intermediate-converting enzyme and the substrate-converting enzyme are produced by microorganisms of the same species. In alternative embodiments, the intermediate-converting enzyme and the substrate-converting enzyme are produced by microorganisms of the different species. In still further embodiments, the concentration level of the intermediate is maintained at a level below that which triggers catabolite repression effects upon the conversion of the intermediate to the end-product. In additional embodiments, concentration level of the intermediate is maintained at a level below that which triggers enzymatic inhibition effects upon the conversion of the intermediate to the end-product. In some preferred embodiments, the intermediate is converted to the end-product at a rate sufficient to maintain the concentration that is less than 0.25%. In yet other embodiments, the substrate is selected from the group consisting of biomass and starch. In some preferred embodiments, the biomass comprises corn solids. In some particularly preferred embodiments, intermediate is selected from the group consisting of hexoses and pentoses. In some embodiments, the hexose is glucose. In some embodiments, the substrate is cooked prior to its use in the present invention, while in other embodiments, the substrate is uncooked prior to its use in the present invention. In yet other embodiments, the step of contacting the substrate and substrate-converting enzyme further comprises bioconverting the substrate to produce the intermediate. In most preferred embodiments, the alcohol end-product is ethanol. In still further embodiments, the step of contacting the substrate and at least one substrate-converting enzyme further comprises providing an amount of the substrate-converting enzyme at a concentration that produces the intermediate at a concentration that is less than or equal to the amount of the intermediate converted by at least one intermediate-converting enzyme. In some additional embodiments, at least one substrate-converting enzyme converts at least 50% of the substrate to the intermediate within 72 hours, while in other embodiments, at least one substrate-converting enzyme converts at least 90% of the substrate to the intermediate within 72 hours, and in some preferred embodiments, at least one substrate-converting enzyme converts at least 95% of the substrate to the intermediate within 72 hours. In still further embodiments, at least one substrate-converting enzyme and at least one intermediate-converting enzyme are obtained from a microorganism selected from the group consisting of *Rhizopus* and *Aspergillus*. In additional embodiments, the substrate-converting and/or intermediate-converting enzyme(s) are provided as a cell-free extract.

In further preferred embodiments, the contacting steps take place in a reaction vessel, including but not limited to vats, bottles, flasks, bags, bioreactors, and any other receptacle suitable for conducting the methods of the present invention.

The present invention further provides methods for producing alcohol as an end-product comprising the steps of contacting a carbon substrate and at least one substrate-converting enzyme to produce an intermediate; and contacting the intermediate with at least one intermediate-converting enzyme, wherein the intermediate is substantially all converted by the intermediate enzyme to the alcohol end-product, and wherein the presence of the end-product does not inhibit the further production of the alcohol end-product. In some preferred embodiments, the intermediate-converting enzyme is a microbial enzyme. In alternative preferred embodiments, the intermediate-converting microbial enzyme is secreted by a microorganism that is in contact with the intermediate. In further preferred embodiments, the substrate-converting enzyme is a microbial enzyme. In still further embodiments, the substrate-converting microbial enzyme is secreted by a microorganism that is in contact with the substrate. In some embodiments, intermediate-converting enzyme and the substrate-converting enzyme are produced by microorganisms of the same species, while in other embodiments, intermediate-converting enzyme and the substrate-converting enzyme are produced by microorganisms of the different species. In yet other embodiments, the substrate is selected from the group consisting of biomass and starch. In some preferred embodiments, the biomass comprises corn solids. In some particularly preferred embodiments, intermediate is selected from the group consisting of hexoses and pentoses. In some embodiments, the hexose is glucose. In some embodiments, the substrate is cooked prior to its use in the present invention, while in other embodiments, the substrate is uncooked prior to its use in the present invention. In some particularly preferred embodiments, the alcohol end-product is ethanol. In still further embodiments, the step of contacting the substrate and at least one substrate-converting enzyme further comprises providing an amount of the substrate-converting enzyme at a concentration that produces the intermediate at a concentration that is less than or equal to the amount of the intermediate converted by at least one intermediate-converting enzyme. In some additional embodiments, at least one substrate-converting enzyme converts at least 50% of the substrate to the intermediate within 72 hours, while in other embodiments, at least one substrate-converting enzyme converts at least 90% of the substrate to the intermediate within 72 hours, and in some preferred embodiments, at least one substrate-converting enzyme converts at least 95% of the substrate to the intermediate within 72 hours. In still further embodiments, at least one substrate-converting enzyme and at least one intermediate-converting enzyme are obtained from a microorganism selected from the group consisting of *Rhizopus* and *Aspergillus*. In additional embodiments, the substrate-converting enzyme is a microbial enzyme. In still further embodiments, the substrate-converting and/or intermediate-converting enzyme(s) are provided as a cell-free extract. In further preferred embodiments, the contacting steps take place in a reaction vessel, including but not limited to vats, bottles, flasks, bags, bioreactors, and any other receptacle suitable for conducting the methods of the present invention.

The present invention further provides methods for producing an alcohol end-product comprising the steps of: contacting a carbon substrate and at least one substrate-converting enzyme to produce an intermediate; and contacting the intermediate with at least one intermediate-converting enzyme, wherein the intermediate is substantially all converted by the intermediate enzyme to the alcohol end-product, and wherein the presence of the substrate does not inhibit the further production of the alcohol end-product. In some preferred embodiments, the intermediate-converting enzyme is a microbial enzyme. In alternative preferred embodiments, the intermediate-converting microbial enzyme is secreted by a microorganism that is in contact with the intermediate. In further preferred embodiments, the substrate-converting enzyme is a microbial enzyme. In still further embodiments, the substrate-converting microbial enzyme is secreted by a microorganism that is in contact with the substrate. In some embodiments, intermediate-converting enzyme and the substrate-converting enzyme are produced by microorganisms of the same species, while in other embodiments, intermediate-converting enzyme and the substrate-converting enzyme are produced by microorganisms of the different species. In yet other embodiments, the substrate is selected from the group consisting of biomass and starch. In some preferred embodiments, the biomass comprises corn solids. In some particularly preferred embodiments, intermediate is selected from the group consisting of hexoses and pentoses. In some embodiments, the hexose is glucose. In some embodiments, the substrate is cooked prior to its use in the present invention, while in other embodiments, the substrate is uncooked prior to its use in the present invention. In some particularly preferred embodiments, the alcohol end-product is ethanol. In still further embodiments, the step of contacting the substrate and at least one substrate-converting enzyme further comprises providing an amount of the substrate-converting enzyme at a concentration that produces the intermediate at a concentration that is less than or equal to the amount of the intermediate converted by at least one intermediate-converting enzyme. In some additional embodiments, at least one substrate-converting enzyme converts at least 50% of the substrate to the intermediate within 72 hours, while in other embodiments, at least one substrate-converting enzyme converts at least 90% of the substrate to the intermediate within 72 hours, and in some preferred embodiments, at least one substrate-converting enzyme converts at least 95% of the substrate to the intermediate within 72 hours. In still further embodiments, at least one substrate-converting enzyme and at least one intermediate-converting enzyme are obtained from a microorganism selected from the group consisting of *Rhizopus* and *Aspergillus*. In additional embodiments, the substrate-converting and/or intermediate-converting enzyme(s) are provided as a cell-free extract. In further preferred embodiments, the contacting steps take place in a reaction vessel, including but not limited to vats, bottles, flasks, bags, bioreactors, and any other receptacle suitable for conducting the methods of the present invention.

BRIEF DESCRIPTION OF THE FIGURES

FIG. 1 provides a graph showing the ethanol results for the experiments described in Example 1.

FIG. 2, Panels A, B and C provide graphs showing the ethanol results from uncooked ground corn fermentation using M1 (Panel A), CU (Panel B), and M1 with DISTIL-LASE® (Panel C).

FIG. 3, Panels A, B and C provide graphs showing the ethanol results obtained in the experiments described in Example 3.

FIG. 4 shows the response of ethanol to the amount of stillage added in both types of mashes.

FIG. 5 shows the glucose profile after 72 hour of fermentation as described in Example 4.

FIG. 6 is a plot of the disaccharides after 72 hours of fermentation with respect to stillage added (See, Example 4).

FIG. 7 shows the levels of the higher sugars (i.e., oligosaccharides greater than disaccharides) (See, Example 4).

FIG. 8 shows the lactic acid level after 72 hours of fermentation (See, Example 4).

FIG. 9 summarizes the glycerol levels after 72 hours of fermentation (See, Example 4).

DESCRIPTION OF THE INVENTION

The present invention provides means for the production of desired end-products of in vitro and/or in vivo bioconversion of biomass-based feed stock substrates, including but not limited to such materials as starch and cellulose. In particularly preferred embodiments, the methods of the present invention do not require gelatinization and/or liquefaction of the substrate. In particularly preferred embodiments, the present invention provides means for the production of ethanol. In some particularly preferred embodiments, the present invention provides means for the production of ethanol directly from granular starch, in which altered catabolite repression is involved.

In particular, the present invention provides means for making ethanol in a manner that is characterized by having altered levels of catabolite repression and enzymatic inhibition, thus increasing the process efficiency. The methods of the present invention comprise the steps of contacting a carbon substrate and a substrate converting enzyme to produce an intermediate; and contacting the intermediate with an intermediate producing enzyme in a reactor vessel, wherein the intermediate is substantially all bioconverted by an end-product producing microorganism. By maintaining a low concentration of the intermediate in a conversion medium, the catabolite repressive or enzymatic inhibitive effects of the intermediate on the process are altered.

The present invention also provides methods in which starches or biomass and hydrolyzing enzymes are used to convert starch or cellulose to glucose. In addition, the present invention provides methods in which these substrates are provided at such a rate that the conversion of starch to glucose matches the glucose feed rate required for the respective fermentative product formation. Thus, the present invention provides key glucose-limited fermentative conditions, as well as avoiding many of the metabolic regulations and inhibitions.

In some preferred embodiments, the present invention provides means for making desired end-products, in which a continuous supply of glucose is provided under controlled rate conditions, providing such benefits as reduced raw material cost, lower viscosity, improved oxygen transfer for metabolic efficiency, improved bioconversion efficiency, higher yields, altered levels of catabolite repression and enzymatic inhibition, and lowered overall manufacturing costs.

As indicated above, there is a great need in the art for methods in which less expensive starting materials than glucose are used to efficiently produce a desired end-product. As described in greater detail herein, the present invention provides methods involving such substrates, including starch (e.g., corn and wheat starch) and biomass.

Starch is a plant-based fermentation carbon source. Corn starch and wheat starch are carbon sources that are much cheaper than glucose carbon feedstock for fermentation. Conversion of liquefied starch to glucose is known in the art and is generally carried out using enzymes such alpha-amylase, pullulanase, and glucoamylase. A large number of processes have been described for converting liquefied starch to the monosaccharide, glucose. Glucose has value in itself, and also as a precursor for other saccharides such as fructose. In addition, glucose may also be fermented to ethanol or other fermentation products. However the ability of the enzymatic conversion of a first carbon source to the intermediate, especially glucose, may be impaired by the presence of the intermediate.

For example, the typical methods used in Japanese sake brewing and alcoholic production use starch without cooking. However, these techniques require some special operations such as acidification of mash (pH 3.5), which prevents contamination of harmful microorganisms. Furthermore, these methods require a longer period of the time for the saccharification and fermentation than the present invention. In addition, these methods require complex process steps such as dialysis of a fermented broth and are too cumbersome to utilize in the general production of products via fermentation.

The use of soluble dextrins and glucose as feed-stock in fermentations have various drawbacks, including high processing cost, problems associated with viscosity and oxygen transfer. In addition, in comparison to the present invention, these methods produce lower yields of the desired products and more problems associated with the formation of by-products. Indeed, the costs of converting starch or biomass to dextrins are substantial and involve high energy input, separate reactor tanks, more time, a detailed bioprocess operation, incomplete saccharification, back-reaction, and enzymes associated with the typical pre-fermentation saccharification step. These problems have led to a number of attempts to provide methods for conversion directly to starch within one reaction vessel or container and at lower temperatures. Biotransformation of a carbohydrate source to 1,3-propanediol in mixed cultures is described in U.S. Pat. No. 5,599,689 (Haynie, et al.). The method described by Haynie et al., involves mixing a glycerol (i.e., an intermediate) producing organism with a diol producing organism (i.e., an end-product), contacting the mixed culture medium with a carbon substrate and incubating the mixed culture medium to produce the desired end-product, 1,3-propanediol. In U.S. Pat. No. 4,514,496, Yoshizuma describes methods that involve maintaining the concentration of the material in the slurry relative the mashing liquid to produce alcohol by fermentation without cooking (i.e., without high temperature liquefaction before saccharization. Nonetheless, these methods lack the efficiency and economical advantages provided by the present invention.

The present invention provides methods for producing end-products, including organic acids (e.g., gluconic acid, ascorbic acid intermediates, succinic acid, citric acid, acetic acid, gluconic acid, and lactic acid), amino acids, antibiotics, enzymes and organic solvents (e.g., 1,3-propanediol, butanediol, and acetone), glycerol, ethanol are provided. In some preferred embodiments, the methods comprise the steps of contacting at least one carbon substrate with at least one substrate converting enzyme to produce at least one intermediate; and contacting at least one intermediate with an intermediate producing enzyme in a reactor vessel, wherein at least one intermediate is substantially completely bioconverted an end-product. In some preferred embodiments, this bioconversion is achieved by microorganisms. By maintaining a low concentration of the intermediate in a conversion medium, the intermediate's catabolite repressive and/or enzymatic inhibitive effects are altered (e.g., reduced). The present invention also provides various levels of intermediate concentration, substrates, intermediates and steps of converting the intermediate to the desired end-product (e.g., ethanol).

DEFINITIONS

Unless defined otherwise herein, all technical and scientific terms used herein have the same meaning as commonly understood by one of ordinary skill in the art to which this invention belongs. Various references (See e.g., Singleton, et al., DICTIONARY OF MICROBIOLOGY AND MOLECULAR BIOLOGY, 2D ED., John Wiley and Sons, New York [1994]; and Hale and Marham, THE HARPER COLLINS DICTIONARY OF BIOLOGY, Harper Perennial, NY [1991]) provide general definitions of many of the terms used herein. Furthermore, all patents and publications, including all sequences disclosed within such patents and publications, referred to herein are expressly incorporated by reference.

Although any methods and materials similar or equivalent to those described herein find use in the practice of the present invention, preferred methods and materials are described herein. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary.

The headings provided herein are not limitations of the various aspects or embodiments of the invention that can be had by reference to the specification as a whole. Furthermore, the terms defined immediately below are more fully defined by reference to the Specification as a whole.

As used herein, the term "carbon substrate" refers to a material containing at least one carbon atom which can be enzymatically converted into an intermediate for subsequent conversion into the desired carbon end-product. Exemplary carbon substrates include, but are not limited to biomass, starches, dextrins and sugars.

As used herein, "biomass" refers to cellulose- and/or starch-containing raw materials, including but not limited to wood chips, corn stover, rice, grasses, forages, perrie-grass, potatoes, tubers, roots, whole ground corn, cobs, grains, wheat, barley, rye, milo, brans, cereals, sugar-containing raw materials (e.g., molasses, fruit materials, sugar cane or sugar beets), wood, and plant residues. Indeed, it is not intended that the present invention be limited to any particular material used as biomass. In preferred embodiments of the present invention, the raw materials are starch-containing raw materials (e.g., cobs, whole ground corns, corns, grains, milo, and/or cereals, and mixtures thereof). In particularly preferred embodiments, the term refers to any starch-containing material originally obtained from any plant source.

As used herein, "starch" refers to any starch-containing materials. In particular, the term refers to various plant-based materials, including but not limited to wheat, barley, potato, sweet potato, tapioca, corn, maize, cassava, milo, rye, and brans. Indeed, it is not intended that the present invention be limited to any particular type and/or source of starch. In general, the term refers to any material comprised of the complex polysaccharide carbohydrates of plants, comprised of amylose and amylopectin, with the formula $(C_6H_{10}O_5)_x$, wherein "x" can be any number.

As used herein, "cellulose" refers to any cellulose-containing materials. In particular, the term refers to the polymer of glucose (or "cellobiose"), with the formula $(C_6H_{10}O_5)_x$, wherein "x" can be any number. Cellulose is the chief constituent of plant cell walls and Is among the most abundant organic substances in nature. While there is a β-glucoside linkage in cellulose, there is an α-glucoside linkage in starch. In combination with lignin, cellulose forms "lignocellulose."

As used herein, the term "corn solids" refers to ground materials from corn, including but not limited to kernels, bran and cobs.

As used herein, "intermediate" refers to a compound that contains at least one carbon atom into which the carbon substrates are enzymatically converted. Exemplary intermediates include, but are not limited to pentoses (e.g., xylose, arabinose, lyxose, ribose, ribulose, xylulose); hexoses (e.g., glucose, allose, altrose, mannose, gulose, idose, galactose, talose, psicose, fructose, sorbose, and tagatose); and organic acids thereof.

As used herein, the term "enzymatic conversion" refers to the modification of a carbon substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the term "starch hydrolyzing enzyme" refers to any enzyme that is capable of converting starch to the intermediate sugar (e.g., a hexose or pentose).

As used herein, "monosaccharide" refers to any compound having an empirical formula of $(CH_2O)_n$, wherein n is 3-7, and preferably 5-7. In some embodiments, the term refers to "simple sugars" that consist of a single polyhydroxy aldehyde or ketone unit. The term encompasses, but is not limited to such compounds as glucose, galactose, and fructose.

As used herein, "disaccharide" refers to any compound that comprises two covalently linked monosaccharide units. The term encompasses, but is not limited to such compounds as sucrose, lactose and maltose.

As used herein, "oligosaccharide" refers to any compound having 2-10 monosaccharide units joined in glycosidic linkages. In some preferred embodiments, the term refers to short chains of monosaccharide units joined together by covalent bonds.

As used herein, "polysaccharide" refers to any compound having multiple monosaccharide units joined in a linear or branched chain. In some preferred embodiments, the term refers to long chains with hundreds or thousands of monosaccharide units. Some polysaccharides, such as cellulose have linear chains, while others (e.g., glycogen) have branched chains. Among the most abundant polysaccharides are starch and cellulose, which consist of recurring glucose units (although these compounds differ in how the glucose units are linked).

As used herein, "culturing" refers to fermentative bioconversion of a carbon substrate to the desired end-product within a reactor vessel. In particularly preferred embodiments, culturing involves the growth of microorganisms under suitable conditions for the production of the desired end-product(s).

As used herein, the term "saccharification" refers to converting a directly unusable polysaccharide to a useful sugar feed-stock for bioconversion or fermentative bioconversion.

As used herein, the term "fermentation" refers to the enzymatic and anaerobic breakdown of organic substances by microorganisms to produce simpler organic products. In preferred embodiments, fermentation refers to the utilization of carbohydrates by microorganisms (e.g., bacteria) involving an oxidation-reduction metabolic process that takes place under anaerobic conditions and in which an organic substrate serves as the final hydrogen acceptor (i.e., rather than oxygen). Although fermentation occurs under anaerobic conditions, it is not intended that the term be solely limited to strict anaerobic conditions, as fermentation also occurs in the presence of oxygen.

As used herein, the terms "substantially all consumed" and "substantially all bioconverted" refer to the maintenance of a low level of intermediate in a conversion medium which adversely affects the enzymatic inhibition, oxygen transfer, yield, byproduct minimization or catabolite repression effects of the intermediate (e.g., a hexose), upon the ability of the intermediate converting enzyme to convert the intermediate to the end-product or another intermediate and/or the ability of the substrate converting enzyme to convert the substrate to the intermediate.

As used herein, the terms "bioconversion" and "bioconverted" refer to contacting a microorganism with the carbon substrate or intermediate, under conditions such that the carbon substrate or intermediate is converted to the intermediate or desired end-product, respectively. In some embodiments, these terms are used to describe the production of another intervening intermediate in in vitro methods in which biocatalysts alone are used. In some preferred embodiments, the terms encompass metabolism by microorganisms and/or expression or secretion of enzyme(s) that achieve the desired conversion.

As used herein, the terms "conversion media" and "conversion medium" refer to the medium/media in which the enzymes and the carbon substrate, intermediate and end-products are in contact with one another. These terms include, but are not limited to fermentation media, organic and/or aqueous media dissolving or otherwise suspending the enzymes and the carbon substrate, intermediate and end-products. In some embodiments, the media are complex, while in other preferred embodiments, the media are defined.

As used herein, the term "end-product" refers to any carbon-source derived molecule product which is enzymatically converted from the intermediate. In particularly preferred embodiments, the methods of the present invention are used in order to produce a "desired end-product" (i.e., the product that is intended to be produced through the use of these methods). In particularly preferred embodiments, the term refers to an alcohol, particularly ethanol.

As used herein, "low concentration" refers to a concentration level of a compound that is less than that would result in the production of detrimental effects due to the presence of the compound. In particularly preferred embodiments, the term is used in reference to the concentration of a particular intermediate below which the detrimental effects of catabolite suppression and/or enzyme inhibition are observed. In some embodiments, the term refers to the concentration level of a particular intermediate above which triggers catabolite repression and/or enzymes inhibition by substrate and/or products.

As used herein, the phrase "maintained at a level below which triggers catabolite repression effects" refers to maintaining the concentration of an intermediate to below that level which triggers catabolite repression.

As used herein, the term "reduces catabolite repression" means conditions under which the effects of catabolite repression are produced. In preferred embodiments, the term refers to conditions in which the intermediate concentration is less than that threshold which triggers catabolite repressive effects.

As used herein, the term "reduces enzyme inhibition" means conditions under which the inhibition of an enzyme is reduced as compared to the inhibition of the enzyme under usual, standard conditions. In preferred embodiments of the present invention, the term refers to conditions in which the concentration of an intermediate, substrate and/or product of the enzyme reaction is less than that threshold which triggers enzyme inhibition.

As used herein, the term "substrate converting enzyme" refers to any enzyme that converts the substrate (e.g., granular starch) to an intermediate, (e.g., glucose). Substrate converting enzymes include, but are not limited to alpha-amylases, glucoamylases, pullulanases, starch hydrolyzing enzymes, and various combinations thereof.

As used herein, the term "intermediate converting enzyme" refers to any enzyme that converts an intermediate (e.g., D-glucose, D-fructose, etc.), to the desired end-product. In preferred embodiments, this conversion is accomplished through hydrolysis, while in other embodiments, the conversion involves the metabolism of the intermediate to the end-product by a microorganism. However, it is not intended that the present invention be limited to any particular enzyme or means of conversion. Indeed, it is intended that any appropriate enzyme will find use in the various embodiments of the present invention.

As used herein, "yield" refers to the amount of end-product or intermediate produced using the methods of the present invention. In some preferred embodiments, the yield produced using the methods of the present invention is greater than that produced using methods known in the art. In some embodiments, the yield refers to the volume of the end-product or intermediate, while in other embodiments, the term is used in reference to the concentration of the end-product or intermediate in a composition.

As used herein, "byproduct formation" refers to the production of products that are not desired. In some preferred embodiments, the present invention provides methods that avoid or reduce the production of byproducts, as compared to methods known in the art.

As used herein, the term "enzymatic inhibition" refers to loss of enzyme activity by either physical or biochemical effects on the enzyme. In some embodiments, inhibition results from the effects of the product formed by the enzyme activity, while in other embodiments, inhibition results from the action of the substrate or intermediate on the enzyme.

As used herein, "enzyme activity" refers to the action of an enzyme on its substrate. In some embodiments, the enzyme activity is quantitated using means to determine the conversion of the substrate to the intermediate, while in other embodiments, the conversion of the substrate to the end-product is determined, while in still further embodiments, the conversion of the intermediate to the end-product is determined.

As used herein, the term "enzyme unit" refers to the amount of enzyme which converts 1 micromole of substrate per minute to the substrate product at optimum assay conditions (unless otherwise noted). In some embodiments, commercially available enzymes (e.g., SPEZYME®, DISTAL- LASE®, OPTIMAX®; Genencor International) find use in the methods of the present invention.

As used herein, the term "glucoamylase unit" (GAU) is defined as the amount of enzyme required to produce one micromole of glucose per minute under assay conditions of 40° C. and pH 5.0 or under the alternative assay conditions of 25° and pH 7.0.

As used herein, the term "glucose oxidase unit" (GOU) is defined as the amount of enzyme required to oxidize one micromole of D-glucose per minute under assay conditions of 25° C. and pH 7.0, to gluconic acid.

As used herein, the term "catalase units" (CU) is defined as the amount of enzyme required to decompose 1 micromole of hydrogen peroxide per minute under assay conditions of 25° C. and pH 7.0.

As used herein, one AG unit (AGU) is the amount of enzyme which splits one micromole of maltose per minute at 25° C. and pH 4.3. In some embodiments of the present invention, a commercially available liquid form of glucoamylase (OPTIDEX® L-400; Genencor International) with an activity of 400 GAU per ml is used. In alternative embodiments, a commercially available liquid form of glucoamylase (AMG NOVO 150) has an activity of 150 AGU per ml finds use.

As used herein, the terms "starch hydrolyzing unit" and "raw starch hydrolyzing unit" (RHU) are defined as being the amount of enzyme required to produce one gram of glucose per minute from starch, under the assay conditions of 25° C. and pH 5.0.

As used herein, "carbon end-product" means any carbon product produced from the carbon intermediate, wherein the substrate contains at least one carbon atom (i.e., a carbon substrate).

As used herein, "carbon intermediate" refers to the carbon-containing compounds that are produced during the conversion of a carbon-containing substrate to a carbon end-product.

As used herein, "enzymatically controlled" means regulating the amount of carbon intermediate produced from the carbon substrate by altering the amount or activity of the enzyme used in the reaction.

As used herein, "microorganism" refers to any organism with cells that are typically considered to be microscopic, including such organisms as bacteria, fungi (yeasts and molds), *rickettsia*, and protozoa. It is not intended that the present invention be limited to any particular microorganism(s) or species of microorganism(s), as various microorganisms and microbial enzymes are suitable for use in the present invention. It is also not intended that the present invention be limited to wild-type microorganisms, as microorganisms and microbial enzymes produced using recombinant DNA technologies also find use in the present invention.

As used herein, "microbial enzyme" refers to any enzyme that is produced by a microorganism. As used herein, a "microbial intermediate-converting enzyme" is an enzyme that converts an intermediate to an end-product, while a "microbial substrate-converting enzyme" is an enzyme that converts a substrate to an intermediate or directly converts a substrate to an end-product (i.e., there is not intermediate compound).

As used herein, the term "ethanologenic microorganism" refers to a microorganism with the ability to convert a sugar or oligosaccharide to ethanol. Ethanologenic microorganisms are known in the art and include ethanologenic bacteria. The microorganisms are ethanologenic by virtue of their ability to express one or more enzymes that individually or together, convert a sugar to ethanol.

As used herein, the terms "ethanol producer" and "ethanol producing organism" refer to any organism or cell that is capable of producing ethanol from a hexose or a pentose. Generally, ethanol producing cells contain an alcohol dehydrogenase and pyruvate decarboxylase.

As used herein, "antimicrobial" refers to any compound that kills or inhibits the growth of microorganisms.

As used herein, the term "linked culture" refers to a fermentation system that employs at least two cell cultures, in which the cultures are added sequentially. In most embodiments of linked systems, a primary culture or a set of primary cultures is grown under optimal fermentation conditions for the production of a desired intermediate (i.e., the intermediate is released into the culture media to produce a "conditioned medium"). Following the fermentation of the primary culture, the conditioned medium is then exposed to the secondary culture(s). The secondary cultures then convert the intermediate in the conditioned media to the desired end-product. In some embodiments of the present invention, the primary cultures are typically glycerol producers and the secondary cultures are 1,3-propanediol producers.

As used herein, "mixed culture" refers to the presence of any combination of microbial species in a culture. In some preferred embodiments, the mixed culture is grown in a reaction vessel under conditions such that the interaction of the individual metabolic processes of the combined organisms results in a product which neither individual organism is capable of producing. It is not intended that the present invention be limited to mixed cultures comprising a particular number of microbial species.

As used herein, "conditioned media" refers to any fermentation media suitable for the growth of microorganisms that has been supplemented by organic byproducts of microbial growth. In preferred embodiments of the present invention, conditioned media are produced during fermentation of linked cultures wherein glycerol producing cells secrete glycerol into the fermentation media for subsequent conversion to 1,3-propanediol.

As used herein, "oxygen uptake rate" ("OUR") refers to the determination of the specific consumption of oxygen within the reactor vessel. Oxygen consumption can be determined using various on-line measurements known in the art. In one embodiment, the OUR (mmol/(liter*hour)) is determined by the following formula: ((Airflow (standing liters per minute)/Fermentation weight (weight of the fermentation broth in kilograms))×supply $O_2$×broth density×(a constant to correct for airflow calibration at 21.1 C instead of standard 20.0 C)) minus ([airflow/fermentation weight]×[offgas $O_2$/offgas $N_2$]×supply $N_2$×broth density×constant).

As used herein, "carbon evolution rate" ("CER") refers to the determination of how much $CO_2$ is produced within the reactor vessel during fermentation. Usually, since no $CO_2$ is initially or subsequently provided to the reaction vessel, any $CO_2$ is assumed to be produced by the fermentation process occurring within the reaction vessel. "Off-gas $CO_2$" refers to the amount of $CO_2$ measured within the reactor vessel, usually by mass spectroscopic methods known in the art.

As used herein, the term "enhanced" refers to improved production of proteins of interest. In preferred embodiments, the present invention provides enhanced (i.e., improved) production and secretion of a protein of interest. In these embodiments, the "enhanced" production is improved as compared to the normal levels of production by the host (e.g., wild-type cells). Thus, for heterologous proteins, basically any expression is enhanced, as the cells normally do not produce the protein.

As used herein, the terms "isolated" and "purified" refer to a nucleic acid or amino acid that is removed from at least one component with which it is naturally associated.

DETAILED DESCRIPTION OF THE INVENTION

The present invention provides means for the production of desired end-products of in vitro and/or in vivo bioconversion of biomass-based feed stock substrates, including but not limited to such materials as starch and cellulose. In particularly preferred embodiments, the methods of the present invention do not require gelatinization and/or liquefaction of the substrate. In particularly preferred embodiments, the present invention provides means for the production of ethanol. In some particularly preferred embodiments, the present invention provides means for the production of ethanol directly from granular starch, in which altered catabolite repression is involved.

In preferred embodiments, the present invention provides dramatic improvements in the process for directly converting a commonly available carbon substrate (e.g., biomass and/or starch) into an intermediate, preferably, an intermediate that is readily convertible into a multitude of desired end-products, including alcohols such as ethanol. In particularly preferred embodiments, the present invention provides means for dramatically improving the processes for directly converting granular starch into glucose, an intermediate readily convertible into an ethanol.

In alternative embodiments, the present invention provides means for dramatic improvements in the process for converting starch or cellulose into glucose, which in turn is converted into the desired end-product. By maintaining the presence of the intermediate at a low concentration within the conversion media, overall efficiency of the production is improved. In some embodiments, enzymatic inhibition and/or catabolite repression, oxygen uptake demand, and/or byproduct formation are reduced. In additional preferred embodiments, the present invention provides means for dramatic improvements in the non-cooking conversion of granular starch into glucose, which in turn is converted into the desired end-product.

In some preferred embodiments, the maintenance of minimal intermediate concentrations is achieved by maintaining the concentration of the intermediate at a low concentration. In one embodiment, the concentration of the intermediate is less than or equal to 0.25% by weight volume of the medium (e.g., 0.25% to 0.00001% by weight volume). In other embodiments, the concentration of the intermediate is less than or equal to 0.20%, 0.10%, 0.05%, or 0.01% by weight volume (e.g., 0.20% to 0.00001%, 0.10% to 0.00001% 0.05% to 0.00001%, 0.01% to 0.00001%, respectively). Alternatively, the intermediate concentration is maintained at less than or equal to a concentration of 2.0 µmolar in the conversion media. In another embodiment, the concentration is maintained at less than or equal to 1.0 µmolar. In still another embodiment, the concentration of the intermediate is maintained at a concentration of less than or equal to 0.75 µmolar. In any event, maintaining a low concentration means maintaining the concentration of the intermediate below the threshold that results in enzyme inhibition (i.e., enzyme inhibitive effects), catabolite repression (i.e., catabolite repressive effects).

In further embodiments, the maintenance of a minimal concentration is achieved by maintaining the rate of conversion of the substrate to the intermediate at less than or equal to the rate of conversion of the intermediate to the end-product. While it is recognized that the conversion of the substrate to the intermediate is necessarily rate limiting for the conversion of the intermediate to the end-product, by providing sufficient intermediate converting enzymes for the conversion of substantially all of the intermediate produced by the first enzymatic conversion from the carbon substrate, substantially all of the intermediate is converted to the end-product as fast as it is converted from the starting substrate to minimize the presence of the intermediate in the conversion medium. Exemplary methods of providing such excessive intermediate conversion include providing an excess of intermediate converting enzyme, increasing the enzyme activity of the intermediate converting enzyme, and/or decreasing the activity of the substrate converting enzyme to convert the intermediate to end-product as quickly as it is converted from the substrate. As the actual rate of conversion is contemplated to vary with the specific end product produced, some variation in the amount and experimentation in determining the amount are contemplated. However guidelines for making these determinations are provided herein.

In some embodiments of the present invention, the conversion or consumption rate of the intermediate was determined by the calculating the amount of organism present in the mixed media, taking into consideration the other physical parameters of the mixed media, and multiplying that amount by the generally known conversion rate. This provides a rate of conversion of the intermediate, (e.g., glucose), to the end-product. In some embodiments, this conversion of the intermediate to the desired end product is by conversion or bioconversion of the intermediate to the end-product by a naturally occurring organism or one mutated to provide such bioconversion. Another embodiment of the conversion from intermediate to end product involves the use of an enzymatic conversion by a known enzyme to the desired end-product using known enzymatic conversion methods. For example, in some embodiments, the conversion of glucose to a desired end product (e.g., propanediol, succinic acid, gluconic acid, lactic acid, amino acid, antimicrobials, ethanol, ascorbic acid intermediates and/or ascorbic acid) is accomplished by the addition of an amount of an enzyme known to convert glucose to the specified end product desired.

Once the conversion rate of the intermediate to the desired end product is determined, the limit of the conversion of the carbon substrate to the intermediate can be determined in the same manner. By calculating the upper limit of the intermediate to end product conversion, the conversion rate of the carbon substrate to intermediate can be determined, the main consideration being that the intermediate concentration levels in the conversion media are maintained at a sufficiently low level to adversely effect the normally catabolite repressive/ enzymatic inhibitory effects of the intermediate. In one embodiment, this is accomplished by maintaining the conversion rate of the intermediate to the end product in excess or equal to the rate of conversion of the carbon substrate to the intermediate. Thus, the present invention provides means for increasing the conversion rate to the end product, as well as means for restricting the conversion of the carbon substrate to the intermediate.

Another method for determining whether the rate of conversion of the intermediate to the end product is greater than or equal to the production of the intermediate from the carbon substrate is to measure the weight percentage of the intermediate in the reactor vessel. The amount of the intermediate present in the reactor vessel can be determined by various known methods, including, but not limited to direct or indirect measurement of the amount of intermediate present in the reactor vessel. Direct measurement can be by periodic assays of the reactor vessel, using assays known to identify the amount of intermediate and or end-product in the vessel. In addition, direct measurement of the amounts of intermediates within the reactor vessel include on-line gas, liquid and/or high performance liquid chromatography methodologies known in the art Indirect measurement of the levels of intermediate or end-products produced can be assessed by the measurement of oxygen uptake or carbon dioxide production, using methods known in the art (e.g., by determining the oxygen uptake rate and/or the carbon evolution rate).

Substrates

The substrates of the present invention are carbon-based compounds that can be converted enzymatically to intermediate compounds. Suitable substrates include, but are not limited to processed materials that contain constituents which can be converted into sugars (e.g., cellulosic biomass, glycogen, starch and various forms thereof, such as corn starch, wheat starch, corn solids and wheat solids). During the development of the present invention good results were obtained with corn starch and wheat starch, although other sources, including starches from grains and tubers (e.g., sweet potato, potato, rice and cassava starch) also find use with the present invention. Various starches are commercially available. For example, corn starches are available from Cerestar, Sigma, and Katayama Chemical Industry Co. (Japan); wheat starches are available from Sigma; sweet potato starch is available from Wako Pure Chemical Industry Co. (Japan); and potato starch is available from Nakari Chemical Pharmaceutical Co. (Japan). A particularly useful carbon substrate is corn starch. In some embodiments of the present invention, granular starch is used in a slurry having a percentage of starch between about 20% and about 35%. Preferably, the starch is in a concentration between about 10% and about 35%. In some particularly preferred embodiments, the range for percent starch is between 30% and 32%. In addition to granular starch, other carbon substrate sources find use in the present invention include, but are not limited to biomass, polysaccharides, and other carbon based materials capable of being converted enzymatically to an intermediate.

Fermentable sugars can be obtained from a wide variety of sources, including lignocellulosic material. Lignocellulose material can be obtained from lignocellulosic waste products (e.g., plant residues and waste paper). Examples of suitable plant residues include but are not limited to any plant material such as stems, leaves, hulls, husks, cobs and the like, as well as corn stover, begasses, wood, wood chips, wood pulp, and sawdust. Examples of paper waste include but are not limited to discarded paper of any type (e.g., photocopy paper, computer printer paper, notebook paper, notepad paper, typewriter paper, and the like), as well as newspapers, magazines, cardboard, and paper-based packaging materials. The conditions for converting sugars to ethanol are known in the art. Generally, the temperature is between about 25° C. and 35° C. (e.g., between 25° and 35°, and more particularly at 30° C.). Useful pH ranges for the conversion medium are provided between about 4.0 and 6.0, between 4.5 and 6.0, and between pH 5.5 and 5.8. However, it is not intended that the present invention be limited to any particular temperature and/or pH conditions as these conditions are dependent upon the substrate(s), enzyme(s), intermediate(s), and/or end-product(s) involved.

Enzymes

In some preferred embodiments of the present invention, enzymes that are substrate-converting enzymes (i.e., enzymes that are able to first convert the carbon substrate into the carbon intermediate), and intermediate converting enzymes (i.e., enzymes that are able to convert the resulting intermediate into an intervening intermediate and/or the desired end-product) both find use in the present invention. Enzymes that find use in some embodiments of the present invention to convert a carbon substrate to an intermediate include, but are not limited to alpha-amylase, glucoamylase, starch hydrolyzing glucoamylase, and pullulanase. Enzymes that find use in the conversion of an intermediate to an end-product depend largely on the actual desired end-product. For example enzymes useful for the conversion of a sugar to 1,3-propanediol include, but are not limited to enzymes produced by *E. coli* and other microorganisms. For example enzymes useful for the conversion of a sugar to lactic acid include, but are not limited to those produced by *Lactobacillus* and *Zymomonas*. Enzymes useful for the conversion of a sugar to ethanol include, but are not limited to alcohol dehydrogenase and pyruvate decarboxylase. Enzymes useful for the conversion of a sugar to ascorbic acid intermediates include, but are not limited to glucose dehydrogenase, gluconic acid dehydrogenase, 2,5-diketo-D-gluconate reductase, and various other enzymes. Enzymes useful for the conversion of a sugar to gluconic acid include, but are not limited to glucose oxidase and catalase.

In some preferred embodiments, the alpha-amylase used in some methods of the present invention is generally an enzyme which effects random cleavage of alpha-(1-4) glucosidic linkages in starch. In most embodiments, the alpha-amylase is chosen from among the microbial enzymes having an E. C. number E. C. 3.2.1.1 and in particular E. C. 3.2.1.1-3. In some preferred embodiments, the alpha-amylase is a thermostable bacterial alpha-amylase. In most particularly preferred embodiments, the alpha-amylase is obtained or derived from *Bacillus* species. Indeed, during the development of the present invention good results were obtained using the SPEZYME® alpha-amylase obtained from *Bacillus licheniformis* (Genencor). In other embodiments, black-koji amylase described in alcoholic fermentation from starch such as corn and cassava without precooking (Ueda et al., J. Ferment. Technol., 50:237-242 [1980]; and Ueda et al, J. Ferment. Technol., 58:237-242 [1980]) find use in the present invention.

As understood by those in the art, the quantity of alpha-amylase used in the methods of the present invention will depend on the enzymatic activity of the alpha-amylase and the rate of conversion of the generated glucose by the end-product converter. Generally an amount between 0.001 and 2.0 ml of a solution of the alpha-amylase is added to 1000 gm of raw materials, although in some embodiments, it is added in an amount between 0.005 and 1.5 ml of such a solution. In some preferred embodiments, it is added in an amount between 0.1 and 1.0 ml of such a solution. In further embodiments, other quantities are utilized. For example, generally an amount between 0.01 and 1.0 kg of SPEZYME® FRED (Genencor) is added to one metric ton of starch. In some embodiments, the enzyme is added in an amount between 0.4 to 0.6 kg, while in other embodiments, it is added in an amount between 0.5 and 0.6 kg of SPEZYME® FRED/metric ton of starch.

In preferred embodiments of the present invention, the glucoamylase is an enzyme which removes successive glucose units from the non-reducing ends of starch. The enzyme can hydrolyze both the linear and branched glucosidic linkages of starch, amylose and amylopectin. In most embodiments, the glucoamylase used in the methods of the present invention are microbial enzymes. In some preferred embodiments, the glucoamylase is a thermostable fungal glucoamylase, such as the *Aspergillus* glucoamylase. Indeed, during the development of the present invention, good results were obtained using the DISTALLASE® glucoamylase derived from *Aspergillus niger* (Genencor). Glucoamylase preparations from *Aspergillus niger* have also been used without the use of precooking (See, Ueda et al, Biotechnol. Bioeng., 23:291 [1981]). Three glucoamylases have been selectively separated from *Aspergillus awamori* var. *kawachi* for use in hydrolyzing starch (See, Hayashida, Agr. Biol. Chem., 39:2093-2099 [1973]). Alcoholic fermentation of sweet potato by *Endomycopsis fibuligoeu* glucoamylase without cooking has also been described (Saha et al., Biotechnol. Bioeng., 25:1181-1186 [1983]). Another enzyme that finds use in the present invention is glucoamylase (EC 3.2.1.3), an enzyme that hydrolyzes the alpha.-1,4-glucoside chain progressively from the non-reducing terminal end. This enzyme also hydrolyzes the alpha-1,6-glucoside chain. Glucoamylase is secreted from fungi of the genera *Aspergillus, Rhizopus* and *Mucor* also find use in the methods of the present invention. These enzymes further find use in glucose production and quantitative determination of glycogen and starch. Glucoamylase preparations obtained from *E. fibuligera* (IFO 0111) have been used to contact sweet potato starch for alcoholic fermentation (See, Saha et al., Biotechnol. Bioeng., 25:1181-1186 [1983]). One of this enzyme's major applications is as a saccharifying agent in the production of ethyl alcohol from starchy materials. However, as with the other glucoamylases described herein, this enzyme also finds use in the methods of the present invention.

Additional glucoamylases that find use in the methods of the present invention include those obtained from the genera *Rhizopus* and *Humicola*, which are characterized as having particularly high productivity and enzymatic activity. Furthermore, in comparison with the glucoamylase derived from other organisms, the *Rhizopus*-derived glucoamylase exhibits a strong action on starch and its enzymological and chemical properties including optimum pH are particularly suitable for the saccharification of cereal starch. Because of these features, the *Rhizopus*-derived glucoamylase is considered to be best suited for alcohol production using non-cooked or low-temperature cooked starch (See, U.S. Pat. Nos. 4,514,496 and 4,092,434). It has been noted that upon the incubation of corn starch with *Rhizopus* glucoamylase, was used in conjunction with *Rhizopus* alpha amylase, the starch degradation by glucoamylase was accelerated. While it is not intended that the present invention be limited to any particular mechanism or theory, it is believed that *Rhizopus* glucoamylase has a stronger degradation activity than *Aspergillus niger* glucoamylase preparations which also contain α-amylase (See, Yamamoto et al., Denpun Kagaku, 37:129-136 [1990]). One commercial preparation that finds use in the present invention is the glucoamylase preparation derived from the Koji culture of a strain of *Rhizopus niveus* available from Shin Nippo Chemical Co., Ltd. Another commercial preparation that finds use in the present invention is the commercial starch hydrolyzing composition M1 is available from Biocon India (Bangalore, India).

As understood by those in the art, the quantity of glucoamylase used in the methods of the present invention depends on the enzymatic activity of the glucoamylase (e.g., DISTILLASE® L-400). Generally, an amount between 0.001 and 2.0 ml of a solution of the glucoamylase is added to 450 gm of a slurry adjusted to 20-35% dry solids, the slurry being the liquefied mash during the saccharification and/or in the hydrolyzed starch and sugars during the fermentation. In some embodiments, the glucoamylase is added in an amount between 0.005 and 1.5 ml of such a solution. In some preferred embodiments, the enzyme is added at an amount between 0.01 and 1.0 ml of such a solution.

As indicated above, pullulanases also find use in the methods of the present invention. These enzymes hydrolyze alpha.-1,6-glucosidic bonds. Thus, during the saccharification of the liquefied starch, pullulanases remove successive glucose units from the non-reducing ends of the starch. This enzyme is capable of hydrolyzing both the linear and branched glucosidic linkages of starch, amylose and amylopectin.

Additional enzymes that find use in the present invention include starch hydrolyzing (RSH) enzymes, including *Humicola* RSH glucoamylase enzyme preparation (See, U.S. Pat. No. 4,618,579). This *Humicola* RSH enzyme preparation exhibits maximum activity within the pH range of 5.0 to 7.0 and particularly in the range of 5.5 to 6.0. In addition, this enzyme preparation exhibits maximum activity in the temperature range of 50° C. to 60° C. Thus, in each of the steps of the present invention in which this enzyme is used, the enzymatic solubilization of starch is preferably carried out within these pH and temperature ranges.

In some embodiments, *Humicola* RSH enzyme preparations obtained from the fungal organism strain *Humicola grisea* var. *thermoidea* find use in the methods of the present invention. In some particularly preferred embodiments, these *Humicola* RSH enzymes are selected from the group consisting of ATCC (American Type Culture Collection) 16453, NRRL (USDA Northern Regional Research Laboratory) 15219, NRRL 15220, NRRL 15221, NRRL 15222, NRRL 15223, NRRL 15224, and NRRL 15225, as well as genetically altered strains derived from these enzymes.

Additional RSH glucoamylases that find use in the methods of the present invention include *Rhizopus* RSH glucoamylase enzyme preparations. In some embodiments, the enzyme obtained from the Koji strain of *Rhizopus niveus* available from Shin Nihon Chemical Co., Ltd., Ahjyo, Japan, under the tradename "CU CONC" is used. Another useful enzyme preparation is a commercial digestive from *Rhizopus* available from Amano Pharmaceutical under the tradename "GLUCZYME" (See, Takahashi et al., J. Biochem., 98:663-671 [1985]). Additional enzymes include three forms of glucoamylase (EC 3.2.1.3) of a *Rhizopus* sp., namely "Gluc1" (MW 74,000), "Gluc2" (MW 58,600) and "Gluc 3" (MW 61,400). Gluc1 was found to be 22-25 times more effective than Gluc2 or Gluc3. Thus, although Gluc2 and Gluc3 find use in the present invention, because Gluc1 tightly binds to starch and has an optimum pH of 4.5, Gluc1 finds particular use in the present invention. An additional RSH glucoamylase enzyme preparation for use in the present invention includes enzyme preparations sold under the designation "M1," available from Biocon India, Ltd., Bangalore, India. M1 is a multifaceted enzyme composition or mixture, as indicated by the high performance liquid chromatography spectra of FIG. 1 and the SDS gel of FIG. 2.

As noted above, in most embodiments, *Humicola* RSH glucoamylase enzyme preparations contain glucoamylase activity as well as a potentiating factor which solubilizes starch. The relative proportions of potentiating factor and glucoamylase activity in other RSH enzyme preparations may vary somewhat. However, with RSH glucoamylase enzyme preparations that find use in the present invention, there is usually ample potentiating factor produced along with the glucoamylase fraction. Accordingly, the activity of the RSH glucoamylase enzyme preparations is defined in terms of their glucoamylase activity.

Glucoamylase activity can also be measured for purposes of this invention in 10 D.E. units for either RSH enzyme preparation or conventional glucoamylase. A "10 D.E. unit" is the amount of either type of enzyme which produces 1 micromole of glucose per minute under the assay conditions. To determine glucoamylase activity for purposes of this invention, one-tenth ml of enzyme preparation, diluted if necessary, containing 0.06 units to 1.1 units is added to 0.9 ml of substrate solution preheated at 50° C. for 5 minutes. The substrate solution consists of 40 parts by volume 0.25M sodium acetate buffer (pH 5.5) and 50 parts by volume 4% by weight 10 D.E. maltodextrin in water. The substrate solution is kept at 50° C. for 5 minutes before the enzyme solution is added. After 10 minutes, the reaction is quenched by pouring into a preheated 16 mm test tube and heating in a 100° C. water bath for 6 minutes. Glucose concentration is determined by any convenient method (e.g., glucose reagent kit No. 15-UV from Sigma Chemical Co. or with an instrument such as the Technicon Autoanalyzer).

A particularly useful enzymatic composition includes a mixture of glucoamylase (e.g., DISTILLASE®) and RSH (e.g., M1). The amount of the glucoamylase useful in this combination is in the range of 0.2 to about 1.0 GAU units of glucoamylase per gram of granular solids. A more useful amount of glucoamylase is between about 0.75 to 0.5 GAU per gram of solids. The range of starch hydrolyzing enzyme (M1) present in this mixture ranges from 0.2 starch hydrolyzing units (RSHU) to about 1.0 RSHU per gram of solids. One particularly useful mixture includes about 0.6 GAU DISTILLASE® per gram of corn solids and 0.2 RSHU M1 per gram of corn solids.

In addition to the use of enzymatic compositions containing the above described enzymes, the present invention provides methods in which a microorganism is exposed to a substrate and uses the substrate to produce the desired end-product. Thus, in some embodiments, contacting the substrate or intermediate with a fungal, bacterial or other microorganism that produces the desired end-product is used to convert the substrate or intermediate to the desired intermediate or end-product.

In preferred embodiments of the present invention, once the carbon source is enzymatically converted to the intermediate, it is converted into the desired end-product by the appropriate methodology. Conversion is accomplished via any suitable method (e.g., enzymatic or chemical). In one preferred embodiment, conversion is accomplished by bioconversion of the intermediate by contacting the intermediate with a microorganism. In alternate preferred embodiments, the respective substrate-converting enzyme and the intermediate-converting enzyme are placed in direct contact with the substrate and/or intermediate. In some embodiments, the enzyme(s) are provided as isolated, purified or concentrated preparations.

In further embodiments, the substrate and/or intermediate are placed in direct contact with a microorganism (e.g., bacterium or fungus) that secretes or metabolizes the respective substrate or intermediate. Thus, the present invention provides means for the bioconversion of a substrate to an end-product. In some embodiments, at least one intermediate compound is produced during this conversion process.

In some embodiments, microorganisms that are genetically modified to express enzymes not normally produced by the wild-type organism are utilized. In some particularly preferred embodiments, the organisms are modified to overexpress enzymes that are normally produced by the wild-type organism.

Indeed, commercially available alpha-amylases and glucoamylases find use in the methods of the present invention in economically realistic enzyme concentrations. Although commonly used fermentation conditions do not utilize optimum temperatures, the pH conditions for fermentation do correspond closely to the optimum pH for commercially available saccharification enzymes (i.e., the glucoamylases). In some embodiments of the present invention, complete saccharification to glucose is favored by the gradual solubilization of granular starch. Presumably, the enzyme is always exposed to low concentrations of dextrin. In addition, the removal of glucose throughout the fermentation maintains a low glucose content in the fermentation medium. Thus, glucoamylase is exposed to low concentration of glucose. In consequence, the glucoamylase is used so effectively that economically feasible dosage levels of glucoamylase are suitable for use in the methods of the present invention (i.e., glucoamylase dosage of 0.05-10.0 GAU/g of starch; and preferably 0.2-2.0 GAU/g starch).

The dosages provided above for glucoamylase only approximate the effective concentration of the enzymatic saccharification activity in the fermentation broth, as an additional proportion of the saccharification activity is contributed by the alpha-amylase. Although it is not intended that the present invention be limited to any particular mechanism or theory, it is believed that the alpha-amylase further widens the holes bored by glucoamylase on starch granules (See, Yamamoto et al., supra). Typically, the use of commercially available alpha-amylases results in the production of significant amounts of sugars, such as glucose and maltose.

Addition of the alpha-amylase from *Aspergillus oryzae* (e.g., FUNGAMYL) to wort has been suggested to the brewing industry. This particular enzyme saccharifies dextrins to maltotriose and maltose. Thus, although the purpose of the alpha-amylase is to liquefy the starch, its saccharification propensity also makes the alpha-amylase some part of the saccharifying enzyme content. It is believed that an alpha amylase is present in the M1 composition.

It is also contemplated that addition of the alpha-amylase from *Aspergillus oryzae* (e.g., CLARASE® L (Genencor International Inc.) to wort will find use in the brewing industry. This particular enzyme saccharifies dextrins to maltotriose and maltose. Thus, although the purpose of the alpha-amylase is to liquefy starch, its saccharification propensity also make the alpha-amylase a portion of the saccharifying enzyme content.

Furthermore, some commercially available glucoamylases contain some alpha-amylase activity. Thus, it is possible (albeit usually not practical) to ferment particulate starch in the presence solely of glucoamylase. However, it is not intended that such embodiments be excluded from the present invention.

Thus, it is also contemplated that commercially available starch hydrolyzing enzymes will find use in the present invention as part of a enzyme mixture which includes starch hydrolyzing enzymes, alpha amylases and glucoamylases.

In most embodiments of the methods of the present invention, an effective amount of alpha-amylase is added to a slurry of particulate starch. Those of skill in the art understand that in addition to the uncertain amount of alpha-amylase activity contributed by glucoamylase, the effective activity of the alpha-amylase may be quite different from the unit activity values given by the supplier. The activity of alpha-amylase is pH dependent, and may be different at the pH range selected for the fermentation (i.e., as compared with the test conditions employed by the suppliers for their reported unit activity values). Thus, some preliminary experiments are contemplated as being sometimes necessary in order establish the most effective dosages for alpha-amylases, including those not explicitly described herein, but find use in the methods of the present invention.

In some most preferred embodiments, the alpha-amylase dosage range for fungal alpha-amylases is from 0.02 GAU/g (Fungal Amylase Units) to 2.0 FAU/g of starch, although in some particularly preferably embodiments, the range is 0.05-0.6 FAU/g. One "FAU" is the amount of enzyme which breaks down 5260 mg of starch per hour under a standardized set of conditions, and corresponds to approximately 25 SKB units (See, Cerial Chem., 16:712-723 [1939]). In most embodiments utilizing *Bacillus* alpha-amylases, the range is 0.01 KNU/g to 0.6 KNU/g, preferably 0.05 to 0.15 KNU/g, the NU (or Novo Unit) being the amount of enzyme which breaks down 5.26 mg of starch per hour under a standardized set of conditions. One KNU corresponds to 1000 NU.

It is contemplated that the uncertainty as to the real activity of both the glucoamylase and the alpha-amylase in the fermenting slurry will require some preliminary investigation into the practice of some embodiments. Optimization considerations include the fact that increasing the alpha-amylase dosage with a constant glucoamylase content, increases the fermentation rate. In addition, increasing the glucoamylase dosage with a constant alpha-amylase content increases the fermentation rate. Holding the dosage of enzyme constant and/or increasing the starch content in the slurry also increase the fermentation rate. Indeed, it is contemplated that in some embodiments, the optimum alpha-amylase dosage well exceeds dosages heretofore recommended for liquefying starch; the optimum glucoamylase may well exceed dosages recommended for saccharifying syrups. However, enzyme dosage levels should not be confused with enzyme usage. Substantial proportions of the enzymes dosed into the starch slurry are available for recovery from the fermentation broth for use anew to ferment granular starch.

A further consideration arising from employment of the enzymes at fermentation temperatures is that although the enzymes exhibit low relative activity (e.g., activity of the alpha-amylase from *B. licheniformis* at fermentation temperatures is not more than about 25% of maximum activity), the low relative activity is counterbalanced by the extended duration of the 48-120 hours of fermentation, and by the extended half-life of enzymes that have not been subjected to elevated temperatures. Indeed, it has been determined that more than 90% of the enzyme activity remains after 72 hours of fermentation. It was also noted that the use of M1 resulted in at least 50% of the starch solids being hydrolyzed after 72 hours, at least 90% hydrolyzed after 72 hours and in some cases, at least 95% hydrolyzed after 72 hours.

The alpha-amylase of *B. licheniformis* (SPEZYME® AA or SPEZYME® FRED enzymes; Genencor) is sufficiently stable to withstand brief exposures to still pot temperatures. Thus, recycle of stillage can be used as a way to recycle alpha-amylase. However, recovery of enzyme in recycled stillage requires care, in avoiding subjecting the fermentation broth to ethanol stripping temperatures that deactivate the enzyme(s). For example, the alcohol may be vacuum stripped from the fermentation broth and such stillage recycled to recover the enzymes suitable for use in subsequent reactions.

However, as earlier described, some RSHs (e.g., the enzyme obtained from *Rhizopus*) are available that convert starch to glucose at non-cooking temperatures (e.g., 25 to 35° C.), reducing the need for exposing the enzymatic composition to still pot temperatures. This reduces the energy costs of converting the carbon substrate to the desired end-product, thereby reducing the overall costs of manufacturing. Thus, these enzymes find particular use in the methods of the present invention.

In preferred embodiments of the present invention, once the carbon source is enzymatically converted to the intermediate, it is converted into the desired end-product by the appropriate methodology. Conversion is accomplished via any suitable method (e.g., enzymatic or chemical). In one preferred embodiment, conversion is accomplished by bioconversion of the intermediate by contacting the intermediate with a microorganism. In alternate preferred embodiments, the respective substrate-converting enzyme and the intermediate-converting enzyme are placed in direct contact with the substrate and/or intermediate. In some embodiments, the enzyme(s) are provided as isolated, purified or concentrated preparations.

The desired end-product can be any product that may be produced by the enzymatic conversion of the substrate to the end-product. In some preferred embodiments, the substrate is first converted to at least one intermediate and then converted from the intermediate to an end-product. For example, hexoses can be bioconverted into numerous products, such as ascorbic acid intermediates, ethanol, 1,3-propanediol, and gluconic acid. Ascorbic acid intermediates include but are not limited to 2,5-diketogluconate, 2 KLG (2-keto-L-gluconate), and 5-KDG (5-keto-D-gluconate). Gluconate can be converted from glucose by contacting glucose with glucose dehydrogenase (GDH). In addition, gluconate itself can be converted to 2-KDG (2-keto-D-gluconate) by contacting gluconate with GDH. Furthermore, 2-KDG can be converted to 2,5-DKG by contacting 2-KDG with 2-KDGH. Gluconate can also be converted to 2-KDG by contacting gluconate with 2KR. Glucose can also be converted to 1,3-propanediol by contacting glucose with *E. coli*. In addition, glucose can be converted to succinic acid by contacting glucose with *E. coli*.

Additional embodiments, as described herein are also provided by the present invention. In one particularly preferred embodiment of the present invention, the end-product is ethanol. In some embodiments in which glucose is an intermediate, it is converted to ethanol by contacting glucose with an ethanologenic microorganism. In contacting the intermediate with an intermediate converting enzyme, it is contemplated that isolated and/purified enzymes are placed into contact with the intermediate. In yet another embodiment, the intermediate is contacted with bioconverting agents such as bacteria, fungi or other organism that takes in the intermediate and produces the desired end-product. In some embodiments, the organism is wild-type, while in other embodiments it is mutated.

Preferred examples of ethanologenic microorganisms include ethanologenic bacteria expressing alcohol dehydrogenase and pyruvate decarboxylase, such as can be obtained with or from *Zymomonas mobilis* (See e.g., U.S. Pat. Nos. 5,028,539, 5,000,000, 5,424,202, 5,487,989, 5,482,846, 5,554,520, 5,514,583, and copending applications having U.S. Ser. No. 08/363,868 filed on Dec. 27, 1994, U.S. Ser. No. 08/475,925 filed on Jun. 7, 1995, and U.S. Ser. No. 08/218, 914 filed on Mar. 28, 1994, the teachings of all of which are hereby incorporated by reference, in their entirety).

In additional embodiments, the ethanologenic microorganism expresses xylose reductase and xylitol dehydrogenase, enzymes that convert xylose to xylulose. In further embodiments, xylose isomerase is used to convert xylose to xylulose. In additional embodiments, the ethanologenic microorganism also expresses xylulokinase, an enzyme that catalyzes the conversion of xylulose to xylulose-5-phosphate. Additional enzymes involved in the completion of the pathway include transaldolase and transketolase. These enzymes can be obtained or derived from *Escherichia coli, Klebsiella oxytoca* and *Erwinia* species (See e.g., U.S. Pat. No. 5,514,583).

In some particularly preferred embodiments, a microorganism capable of fermenting both pentoses and hexoses to ethanol are utilized. For example in some embodiments, a recombinant organism which inherently possesses one set of enzymes and which is genetically engineered to contain a complementing set of enzymes is used (See e.g., U.S. Pat. Nos. 5,000,000, 5,028,539, 5,424,202, 5,482,846, 5,514,583, and WO 95/13362). In some embodiments, particularly preferred microorganisms include *Klebsiella oxytoca* P2 and *E. coli* KO11.

In some embodiments, supplements are added to the nutrient medium (i.e., the culture medium), including, but not limited to vitamins, macronutrients, and micronutrients. Vitamins include, but are not limited to choline chloride, nicotinic acid, thiamine HCl, cyanocobalamin, p-aminobenzoic acid, biotin, calcium pantothenate, folic acid, pyridoxine.HCl, and riboflavin. Macronutrients include, but are not limited to $(NH_4)_2SO_4$, $K_2HPO_4$, NaCl, and $MgSO_4.7H_2O$. Micronutrients include, but are not limited to $FeCl_3.6H_2O$, $ZnCl_2.4H_2O$, $CoCl_2.6H_2O$, molybdic acid (tech), $CuCl_3.2H_2O$, $CaCl_2.2H_2O$, and $H_3BO_3$.

Media and Carbon Substrates

The conversion media in the present invention must contain suitable carbon substrates. Suitable carbon substrates include, but are not limited to biomass, monosaccharides (e.g., glucose and fructose), disaccharides (e.g., lactose and sucrose), oligosaccharides, polysaccharides (e.g., starch and cellulose), as well as mixtures thereof, and unpurified mixtures from renewable feedstocks such as cheese whey permeate, cornsteep liquor, sugar beet molasses, and barley malt. In additional embodiments, the carbon substrate comprises one-carbon substrates such as carbon dioxide, or methanol for which metabolic conversion into key biochemical intermediates has been demonstrated.

Although it is contemplated that all of the above mentioned carbon substrates and mixtures thereof will find use in the methods of the present invention, preferred carbon substrates include monosaccharides, disaccharides, oligosaccharides, polysaccharides, and one-carbon substrates. In more particularly preferred embodiments, the carbon substrates are selected from the group consisting of glucose, fructose, sucrose and single carbon substrates such as methanol and carbon dioxide. In a most particularly preferred embodiment, the substrate is glucose.

As known in the art, in addition to an appropriate carbon source, fermentation media must contain suitable nitrogen source(s), minerals, salts, cofactors, buffers and other components suitable for the growth of the cultures and promotion of the enzymatic pathway necessary for the production of the desired end-product (e.g., glycerol). In some embodiments, (II) salts and/or vitamin $B_{12}$ or precursors thereof find use in the present invention.

Culture Conditions

Typically, cells are grown at approximately 30° C. in appropriate media. Preferred growth media utilized in the present invention include common commercially prepared media such as Luria Bertani (LB) broth, Sabouraud Dextrose (SD) broth or Yeast Malt Extract (YM) broth. However, other defined or synthetic growth media may also be used, as appropriate. Appropriate culture conditions are well-known to those in the art.

In some embodiments, agents known to modulate catabolite repression directly or indirectly (e.g., cyclic adenosine 2':3'-monophosphate or cyclic adenosine 2':5'-monophosphate), are incorporated into the reaction media. Similarly, the use of agents known to modulate enzymatic activities (e.g., sulphites, bisulphites and alkalis) that lead to enhancement of glycerol production also find use in conjunction with or as an alternative to genetic manipulations.

Suitable pH ranges for fermentation are between pH 5.0 to pH 9.0; while the range of pH 6.0 to pH 8.0 is particularly preferred for the initial conditions of the reaction system. Furthermore, reactions may be performed under aerobic, microaerophilic, or anaerobic conditions, as suited for the organism utilized.

Batch and Continuous Fermentations

In some preferred embodiments, the present process uses a batch method of fermentation. A classical batch fermentation is a closed system, wherein the composition of the media is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells moderate through a static lag phase to a high growth log phase and finally to a stationary phase where growth rate is diminished or halted. If untreated, cells in the stationary phase eventually die. In general, cells in log phase are responsible for the bulk of production of end product or intermediate.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

It is also contemplated that the methods of the present invention are adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen level is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology.

In some embodiments, the present invention is practiced using batch processes, while in other embodiments, fed-batch or continuous processes, as well as any other suitable mode of fermentation are used. Additionally, in some embodiments, cells are immobilized on a substrate as whole-cell catalysts and are subjected to fermentation conditions for the appropriate end-product production.

Identification and Purification of the End-Product

Methods for the purification of the end-product from fermentation media are known in the art. For example, propanediols can be obtained from cell media by subjecting the reaction mixture to extraction with an organic solvent, distillation and column chromatography (See e.g., U.S. Pat. No. 5,356,812). A particularly good organic solvent for this process is cyclohexane (See, U.S. Pat. No. 5,008,473).

In some embodiments, the end-product is identified directly by submitting the media to high pressure liquid chromatography (HPLC) analysis. One method of the present invention involves analysis of fermentation media on an analytical ion exchange column using a mobile phase of 0.01 N sulfuric acid in an isocratic fashion.

Identification and Purification of the Enzymes

The enzyme levels in the media can be measured by enzyme assays. For example in the manufacture of 1,3-propanediol, the levels of expression of the proteins G3PDH and G3P phosphatase are measured by enzyme assays. The G3PDH activity assay relies on the spectral properties of the cosubstrate, NADH, in the DHAP conversion to G-3-P. NADH has intrinsic UV/vis absorption and its consumption can be monitored spectrophotometrically at 340 nm. G3P phosphatase activity can be measured by any method of measuring the inorganic phosphate liberated in the reaction. The most commonly used detection method used the visible spectroscopic determination of a blue-colored phosphomolybdate ammonium complex.

Thus, although there are various superficial resemblances between the methods known in the art and the methods of the present invention, the present invention provides more comprehensive objectives that are reflected in a great number of detail features believed to be unique to practice of this invention, including notably enzyme recycling, biomass and starch recycling.

Recovery

Overall, recovery of enzymes in recycled stillage requires care, in order to avoid subjecting the conversion media to temperatures that deactivate the enzymes. In one example, for the recovery of ethanol, the alcohol is vacuum stripped from the fermentation broth and the stillage is recycled, in order to recover the enzymes. In embodiment, enzymes are recovered through the use of ultrafiltration or an electrodialysis device and recycled.

Process Considerations

As indicated above, fermentation of granular starch slurry has completely different characteristics than fermentation of a syrup. Generally, a concentration of about 20% solids in solution is considered the maximum sugar content in a fermentation medium, as higher concentrations create difficulties at the onset and at the end of fermentation. However, no similar limits exist in the fermentation of a starch slurry. The concentration of starch in the slurry may vary from 10-35%, with no discernable consequences at the onset of fermentation. Increasing starch concentration (e.g., at constant enzyme dosages) speeds up the bioconversion rate, or conversely, allows for lowering the enzyme dosages required to achieve a given bioconversion rate. In any event fermenting until the broth has 7-10% alcohol, as is prevalent in the fermentation arts, is still possible. The excess (i.e., residual) granular starch may be recovered, along with substantial amounts of enzymes and subjected to renewed fermentation. Thus, control over starch concentration is a major process parameter for practice of this invention.

In one preferred embodiment, means for bioconversion and fermentation of a granular starch slurry having 10-35% starch by weight are provided. In some preferred embodiments, fermentation of a 10-35% starch slurry with *E. coli* results in the production of residual starch when fermentation has proceeded to the intended organic acid or 1,3-propane diol content levels. However, this reaction is dependent on the microorganism and bioprocessing conditions used and, therefore, recycling of the enzymes on the starch particles occurs when the residual starch is again fermented. However, even when a 25-35% starch slurry is fermented, in preferred embodiments, the fermentation is halted before complete disappearance of the granular starch, for fermentation anew. Thus, recycling of starch is a facile way to recover enzymes for reuse.

In an alternative embodiment, means for fermentation of a granular starch slurry of 25-25% by weight are provided. Fermenting a 25-35% starch slurry with common baker's yeast will invariably result in residual starch when fermentation has proceeded to the intended alcohol content levels (e.g., 7-10%), dependent on the microorganism used and the recycling of the enzymes on the starch particles occurs when the residual starch is again fermented. However, it is not intended that the present invention be limited to this range, as other weight percentages will find use in the present invention, depending upon the substrate and/or enzyme system utilized in the methods. For example, in some embodiments, a granular starch slurry of 10-35% by weight is preferred. A particularly useful microorganism is one that is resistant to the alcohol produced by the process.

In one preferred embodiment of the present invention, the (granular) starch and microorganisms are removed together (e.g., by centrifugation or filtration). This removed starch and microorganisms are mixed with fresh granular starch and additional aliquot(s) of enzyme(s) as needed, to produce a fermentation charge for another fermentation run.

In another embodiment, bioconversion and fermentation of a corn-stover slurry having 10-35% cellulosics by weight is provided. In one embodiment, fermenting a 10-35% cellulosic slurry with *E. coli* results in residual cellulosic when fermentation has proceeded to the intended organic acid or 1,3-propane diol content levels. This reaction is dependent upon the microorganism and bioprocessing conditions used. As above, recycling of the enzymes on the cellulosics occurs when the residual corn-stover is again fermented. However, even when a 25-35% cellulosics slurry is fermented, in some preferred embodiments, the fermentation is halted before the complete disappearance of the stover, for fermentation anew. Thus, recycling stover is a facile way to recover enzymes for reuse.

In yet another preferred embodiment, the granular starch or corn stover and microorganisms are removed together (e.g., by centrifugation or filtration). This mixture of removed granular starch or corn stover and microorganisms is mixed with fresh granular starch or corn stover and additional aliquot(s) of enzyme(s) as needed, to produce a fermentation charge for another fermentation run.

As recognized by those of skill in the art, engineering trade-offs are contemplated in arriving at optimum process details; these trade-offs are contemplated to vary, depending upon each particular situation. Nonetheless, the methods provided herein provide the necessary teachings to make such trade-offs to obtain optimum processes. For example, to achieve the most rapid fermentation reasonable, high starch or cellulosic content, and high enzymes dosage are indicated. But, the consequential rapid fermentation tails off into generation of a level of nutrients in the fermentation broth, when then dictates recovery of the nutrients, or, alternatively that fermentation be halted at a relatively low end-product (e.g., alcohol) content. However, in situations where relatively low fermentation rates are acceptable, then (with high starch content slurries) enzyme dosage is relatively low and nutrient losses are held to levels heretofore accepted by the fermentation arts. In cases where maximum yield of end-product (e.g., alcohol) is a principal objective, then low starch content slurries, moderate alpha-amylase dosage, and high glucoamylase dosage find use in the present invention. However, it is not intended that the present invention be limited to any particular method design.

As indicated herein, the present invention saves considerable thermal energy. However, just as the starting substrate (e.g., starch) is never subjected to the thermal conditions used for liquefactions, the substrate is not thermally sterilized. Thus, it is contemplated that is some embodiments, the starting substrate (e.g., granular starch) adds contaminating microorganisms to the fermentation medium. Thus, in some embodiments, it is advantageous to seed the fermentation medium with a large number of the product-producing microorganisms that are associated with recycled substrate (e.g., starch). By greatly outnumbering the contaminants, the recycled microorganisms overwhelm any contaminating microorganisms, thereby dominating the fermentation, resulting in the production of the desired end-product. Thus, in some embodiments, the method involves seeding the fermentation medium with the great number of the ethanol producing microorganism that are likely to accompany the recycled granular starch. Through their great numbers, the recycled microorganisms overwhelm any contaminating microorganisms, thereby dominating the fermentation, as is, of course, desired.

In some embodiments, the quantities of yeast initially charged into the fermentation vat may be in accord with prior art practices for ethanol fermentation, and can vary widely since the yeast cells will multiply during the course of the fermentation. Recycling of yeast cells is not necessary, although may be performed. In some embodiments, the yeast is removed from the residual starch particles prior to recycling of the residual starch. However, it is noted once again that practice of the present invention does not necessarily require a thermal treatment of the starch (i.e., thermal conditions that would heat sterilize the starch). Thus, as with bacteria, it is advisable in some embodiments of the present invention to charge relatively large proportions of yeast cells into the fermentation in order to help overcome the likelihood of (inadvertent) contamination. In addition, in some embodiments, antimicrobials are added to the fermentation medium to suppress growth of contaminating microorganisms. In further embodiments, cold sterilization techniques are utilized with the materials involved in the methods.

In most preferred embodiments, the practice of the present invention controls the fermentation rate by releasing metabolizable sugars to the microorganisms (e.g., yeast) at a controlled rate and maintaining the concentration of the intermediate (e.g., glucose) at a level that does not trigger enzyme inhibition or catabolite repression. This approach is very different from what was done prior to the development of the present invention. Indeed, the prior art suggests treating solid starch with enzymes prior to fermentation and/or including enzymes in the fermentation medium to conserve energy and/or to improve fermentation efficiency. However, these teachings do not alter the character of the fermentation so as to avoid the adverse effects of catabolite repression and/or enzymatic inhibition. The present invention also provide means to counter the adverse effects of producing undesired by-products from glucose. The present invention also provides means to conserve energy, particularly in comparison with prior art methods involving high temperature starch liquefaction. Indeed, the present invention provides means to conserve more thermal energy than other methods. The present invention provides methods that operate with high fermentation efficiency, in part because product losses due to starch retrogradation, incomplete saccharification, and incomplete fermentation of fermentables are reduced. The ability to tailor the fermentation rate through control of starch concentration and enzyme content and proportions includes the capability of creating a fermentation broth product with minimal carbohydrate content.

As indicated above, in some embodiments, the quantities of microorganisms and enzymes initially charged into the fermentation vat or bioreactor are in accord with prior art practices for the fermentation or bioconversion of various products. These quantities will vary, as the microbial cells multiply during the course of the fermentation whereas enzymes used for bioconversion will have a limited half-life. Although in some embodiments, recycling of microorganisms is utilized, in many embodiments, it is not required for the practice of the present invention. In contrast, in particularly preferred embodiments, it is desirable to recycle enzymes (although it is not intended that the present invention be limited to methods which require the recycling of enzymes).

Thus, in some embodiments, the microbes are removed from the residual starch or biomass particles prior to recycling of the residual starch or biomass. However, it is again noted that practice of the present invention does not necessarily require thermal treatment of the starting substrate (e.g., starch). Thus, in some embodiments, the starting substrate is heat-sterilized, while in other embodiments, it is not. Therefore, in some embodiments, the fermentation/bioconversion is conducted in the presence of a relatively large proportion of microorganisms, in order to overcome the effects of any contamination. In alternative embodiments, antimicrobials are added to the fermentation medium to suppress growth of contaminating microorganisms. In additional embodiments, cold sterilization techniques, UV radiation, 65° C. pasteurization are used to sterilize the starting (e.g, substrate) materials. However, biomass poses no problem regarding sterilization of fermentation vats or bioreactors.

Use of starch as the starting material does not only address the above shortcomings of currently used methods, but has three additional significant benefits in terms of the raw material cost of corn starch vs. D-glucose, reduction of substrate and/or product based inhibition of enzymes employed in the bioconversion, and a concomitant significant reduction in the requirement of high enzyme dosages.

Various other examples and modifications of the description and Examples are apparent to a person skilled in the art after reading the disclosure without departing from the spirit and scope of the invention; it is intended that all such examples or modifications be included within the scope of the appended claims. All publications and patents referenced herein are hereby incorporated by reference in their entirety.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the experimental disclosure which follows, the following abbreviations apply: wt % (weight percent); ° C. (degrees Centigrade); rpm (revolutions per minute); $H_2O$ (water); $dH_2O$ (deionized water); (HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); psi (pounds per square inch); sec (seconds); min(s) (minute/minutes); hr(s) (hour/hours); Q.S. and q.s. (quantity sufficient); OD (optical density); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); Cerestar (Cerestar, a Cargill, inc., company, Minneapolis, Minn.); SDS (sodium dodecyl sulfate); Tris(tris(hydroxymethyl)aminomethane); w/v (weight to volume); v/v (volume to volume); ATCC (American Type Culture Collection, Rockville, Md.); Difco (Difco Laboratories, Detroit, Mich.); GIBCO BRL or Gibco BRL (Life Technologies, Inc., Gaithersburg, Md.); Genencor (Genencor International, Inc., Palo Alto, Calif.); Shin Nihon (Shin Nihon, Japan); BioRad (BioRad Laboratories, Hercules, Calif.); and LeSaffre (LeSaffre Yeast Corporation, Milwaukee, Wis.).

In the following Examples, additional various media and buffers known to those in the art were used, including the following:

Example 1

Fermentation of Non-Cooked Corn Mash

In this Example, experiments conducted to compare starch hydrolyzing enzyme activity with a glucoamylase on uncooked starch are described.

Fermentation experiments were carried out in 250 ml flasks that were incubated in a 30° C. shaker water bath. For this experiment 112 gm of 32.1% ground corn slurry containing 0.5% dry corn steep was placed in 250 ml flasks. The pH of the slurry was about 5.7, which required no further adjustment. The desired enzymes (DISTILLASE®) or Sumizyme CU; Shin Nihon) were added, along with 0.37 gm of Red Star active dry yeast (LaSaffre) to start the saccharification and fermentation. During the fermentation a sample of the beer was centrifuged and 0.5 ml of supernatant was added to a test tube containing 0.05 ml of 1.1 N $H_2SO_4$ containing 5% glutaraldehyde to terminate both the fermentation and enzyme action. The sample was then diluted with 5.0 ml water and then subjected to HPLC analysis on Bio Rad HPX-87H column. The results are shown in Table 1 below.

TABLE 1

Fermentation of Uncooked Ground Corn Comparing Sumizyme CU With Distillase Fermentation at 30° C. With enzyme dosage as GAU per gm of corn.

| Flask | Enzyme | Hours | % W/V % DP > 2 | % W/V DP – 2 | % W/V DP – 1 | % W/V Lactic | % W/V Glycerol | % V/V Ethanol |
|---|---|---|---|---|---|---|---|---|
| 1 | 0.20 GAU/g CU | 24 | 0.27 | 0 | 0.02 | 0.12 | 0.66 | 8.91 |
| | | 48 | 0.29 | 0 | 0 | 0.06 | 0.71 | 13.68 |
| | | 72 | 0.30 | 0 | 0 | 0.02 | 0.59 | 15.07 |
| 2 | 0.20 GAU/g Dist | 24 | 0.25 | 0 | 0 | 0.13 | 0.28 | 3.05 |
| | | 48 | 0.20 | 0 | 0 | 0.37 | 0.26 | 4.59 |
| | | 72 | 0.19 | 0 | 0 | 0.49 | 0.24 | 6.10 |
| 3 | 0.40 GAU/g Dist | 24 | 0.20 | 0 | 0 | 0.09 | 0.34 | 4.59 |
| | | 48 | 0.21 | 0 | 0 | 0.12 | 0.38 | 7.24 |
| | | 72 | 0.17 | 0 | 0 | 0.11 | 0.38 | 9.45 |
| 4 | 0.75 GAU/g Dist | 24 | 0.22 | 0 | 0 | 0.08 | 0.40 | 5.51 |
| | | 48 | 0.20 | 0 | 0 | 0.06 | 0.44 | 9.54 |
| | | 72 | 0.21 | 0 | 0 | 0.03 | 0.45 | 12.13 |
| 5 | 1.00 GAU/g Dist | 24 | 0.24 | 0 | 0 | 0.11 | 0.49 | 6.38 |
| | | 48 | 0.22 | 0 | 0 | 0.13 | 0.41 | 10.64 |
| | | 72 | 0.18 | 0 | 0 | 0.07 | 0.61 | 13.29 |

CU = Sumizyme CU from Shin Nihon
Dist = Distillase L-400

As indicated in the Table 1, little if any detectable glucose is found in the beer, which indicated as the starch is being hydrolyzed it quickly was converted to ethanol by the yeast. FIG. 1 provides a graph showing the ethanol content of the various tests.

These results could show that a starch hydrolyzing enzyme could convert the uncooked starch much more efficiently than DISTILLASE®. The rate of fermentation seems more related to the RSU activity. The 0.2 GAU/gm level of CU corresponds to 0.590 RHU/gm, while the 1.0 GAU/gm level of DISTILLASE® corresponds to only 0.108 RHU/gm. The RHU/GAU ratio for DISTILLASE® is 0.54 whereas the RHU/GAU ratio for CU is 2.98, which shows an enzyme with a high RHU/GAU ratio can better hydrolyze uncooked starch.

Example 2

Fermentation of Ground Corn Slurry

In these experiments, the same procedure was used for this experiment as in Example 1, except that 35.9% ground corn slurry was used (instead of corn mash), and prior to starting the fermentation the slurry was placed in a 65° C. water for one hour as a pasteurization step. No observed gelatinization of the slurry was observed. The enzymes tested were Sumizyme CU (Example 1), a *Rhizopus* glucoamylase preparation (M1) from Biocon assayed at 178 GAU/gm and 277 RHU/gm, and DISTILLASE® L-400 (Dist.) at 361 GAU/gm and 196 RHU/gm. Table 2 provides the conditions used for this study, and also summarizes the results.

TABLE 2

Fermentation Uncooked Starch With Separate And Enzyme Combinations

| Sample | Enzyme | Level | Enzme | Level | Hours | % W/V DP > 2 | % W/V DP − 2 | % W/V DP − 1 | % W/V Lactic | % W/V Glycerol | % V/V Ethanol |
|---|---|---|---|---|---|---|---|---|---|---|---|
| 1 | M1 | .20 GAU/g | | | 24 | 0.40 | 0.04 | 0.02 | 0.17 | 0.67 | 8.66 |
| 1 | | | | | 48 | 0.35 | 0.02 | 0.00 | 0.10 | 0.74 | 12.28 |
| 1 | | | | | 72 | 0.36 | 0.01 | 0.00 | 0.04 | 0.76 | 14.02 |
| 2 | M1 | .50 GAU/g | | | 24 | 0.42 | 0.03 | 0.01 | 0.13 | 0.80 | 11.91 |
| 2 | | | | | 48 | 0.41 | 0.04 | 0.00 | 0.04 | 0.82 | 15.24 |
| 2 | | | | | 72 | 0.54 | 0.03 | 0.00 | 0.02 | 0.84 | 15.23 |
| 3 | M1 | .75 GAU/g | | | 24 | 0.42 | 0.03 | 0.01 | 0.12 | 0.86 | 12.43 |
| 3 | | | | | 48 | 0.53 | 0.02 | 0.01 | 0.06 | 0.91 | 15.30 |
| 3 | | | | | 72 | 0.55 | 0.03 | 0.01 | 0.03 | 0.94 | 15.43 |
| 4 | CU | .20 GAU/g | | | 24 | 0.34 | 0.03 | 0.10 | 0.14 | 0.92 | 10.59 |
| 4 | | | | | 48 | 0.35 | 0.07 | 0.05 | 0.09 | 1.03 | 14.96 |
| 4 | | | | | 72 | 0.40 | 0.04 | 0.04 | 0.04 | 1.04 | 15.63 |
| 5 | CU | .50 GAU/g | | | 24 | 0.37 | 0.13 | 0.80 | 0.13 | 0.96 | 12.20 |
| 5 | | | | | 48 | 0.45 | 0.24 | 1.15 | 0.08 | 1.05 | 14.96 |
| 5 | | | | | 72 | 0.45 | 0.25 | 1.46 | 0.07 | 1.08 | 14.96 |
| 6 | CU | .75 GAU/g | | | 24 | 0.43 | 0.16 | 1.15 | 0.13 | 0.97 | 12.69 |
| 6 | | | | | 48 | 0.51 | 0.30 | 2.19 | 0.08 | 1.05 | 14.90 |
| 6 | | | | | 72 | 0.51 | 0.33 | 2.67 | 0.07 | 1.08 | 14.83 |
| 7 | M1 | .20 GAU/g | Dist | .2 GAU/g | 24 | 0.41 | 0.04 | 0.02 | 0.14 | 0.71 | 9.19 |
| 7 | | | | | 48 | 0.35 | 0.01 | 0.00 | 0.07 | 0.75 | 13.06 |
| 7 | | | | | 72 | 0.40 | 0.02 | 0.00 | 0.02 | 0.78 | 15.20 |
| 8 | M1 | .20 GAU/g | Dist | .6 GAU/g | 24 | 0.33 | 0.04 | 0.03 | 0.15 | 0.77 | 9.56 |
| 8 | | | | | 48 | 0.39 | 0.02 | 0.00 | 0.09 | 0.84 | 13.56 |
| 8 | | | | | 72 | 0.38 | 0.03 | 0.00 | 0.04 | 0.86 | 15.02 |
| 9 | M1 | .20 GAU/g | Dist | 2.0 GAU/g | 24 | 0.30 | 0.03 | 0.03 | 0.13 | 0.82 | 10.46 |
| 9 | | | | | 48 | 0.33 | 0.02 | 0.01 | 0.08 | 0.89 | 14.66 |
| 9 | | | | | 72 | 0.38 | 0.03 | 0.01 | 0.03 | 0.90 | 15.74 |

The ethanol results from the fermentations with M1 and CU are plotted in FIGS. 2A and 2B. At the 0.2 GAU/gm level for M1 the rate and yield of ethanol is less than the 0.5 and 0.75 levels indicating the 0.2 level is enzyme limiting. The 0.5 and 0.75 levels of M1 seem to give very similar results indicating that enzyme is no longer limiting. The results from CU similarly shows that the 0.2 enzyme level is somewhat limiting the fermentation, but is faster than 0.2 GAU/gm for M1 results. This indicates that the RHU activity is a better parameter that indicates the hydrolysis of uncooked starch. CU has about twice the RHU activity per GAU as does M1, and CU is seen to hydrolyze the uncooked starch faster at similar GAU levels. At the 0.5 and 0.75 GAU/gm dosage excess glucose is observed particularly at the higher enzyme level. Actually it appears that starch hydrolyzing rate is faster than the fermentation rate. These results also show that at around 15% ethanol, the ethanol seems to become toxic to the yeast since the fermentations appeared to stop.

The graph provided at FIG. 2, Panel C shows the ethanol results from the fermentations where M1 was added to DISTILLASE®. As the results show, adding DISTILLASE® to a low level of M1, 0.2 GAU/gm, both the rate and yield of ethanol increased improving the performance of M1. These results show that by adding a glucoamylase preparation with a GSH ratio greater than 1.5 to DISTILLASE®, which has only a GSH ratio less than 0.6, can hydrolyze uncooked starch so that ethanol can be made by a process that eliminates the cooking step.

Example 3

Comparison of Cooked and Uncooked Corn Mash

In these experiments, fermentations were conducted similar to that described in Example 1, except 83 gm of 28.9% ground corn slurry were placed in 250 ml bottles containing a magnetic bar. The bottles were placed on a submersion magnetic stirrer in a 30° C. water bath so that the mash was gently mixed during the fermentation. Combinations of DISTILLASE® and M1 were tested as shown in Table 3. These fermentation were started with 0.27 gm of dry yeast. After the fermentation, the beer was dried in a 65° C. forced air oven to obtain what was considered the DDGS (Distillers Dry Grains plus the Solubles). In this manner a quantitative estimate of the DDGS was obtained, and the starch contend of the DDGS was obtained by a starch analysis technique. The HPLC profiles of the fermentations are also shown in Table 3.

TABLE 3

| | | | | HPLC Profile | | | | | |
|---|---|---|---|---|---|---|---|---|---|
| Trial | M1 GAU/g | Dist. GAU/g | Hours | % W/V DP > 2 | % W/V DP − 2 | % W/V DP − 1 | % W/V Lactic | % W/V Glycerol | % V/V Ethanol |
| 1 | 0.10 | 0.00 | 24 | 0.23 | 0 | 0 | 0.08 | 0.28 | 3.40 |
| 1 | | | 48 | 0.26 | 0 | 0 | 0.46 | 0.56 | 5.66 |
| 1 | | | 72 | 0.27 | 0 | 0 | 0.62 | 0.33 | 6.95 |
| 2 | 0.10 | 0.20 | 24 | 0.24 | 0 | 0 | 0.11 | 0.41 | 5.70 |
| 2 | | | 48 | 0.27 | 0 | 0 | 0.09 | 0.46 | 9.21 |
| 2 | | | 72 | 0.32 | 0 | 0 | 0.04 | 0.48 | 11.44 |
| 3 | 0.10 | 0.40 | 24 | 0.19 | 0 | 0 | 0.14 | 0.52 | 6.87 |

TABLE 3-continued

| | | | HPLC Profile | | | | | |
|---|---|---|---|---|---|---|---|---|
| Trial | M1 GAU/g | Dist. GAU/g | Hours | % W/V DP > 2 | % W/V DP – 2 | % W/V DP – 1 | % W/V Lactic | % W/V Glycerol | % V/V Ethanol |
| 3 | | | 48 | 0.26 | 0 | 0 | 0.12 | 0.61 | 10.87 |
| 3 | | | 72 | 0.27 | 0 | 0 | 0.05 | 0.63 | 12.98 |
| 4 | 0.10 | 0.60 | 24 | 0.22 | 0 | 0 | 0.15 | 0.59 | 7.79 |
| 4 | | | 48 | 0.26 | 0 | 0 | 0.12 | 0.67 | 11.93 |
| 4 | | | 72 | 0.29 | 0 | 0 | 0.05 | 0.69 | 13.63 |
| 5 | 0.10 | 1.00 | 24 | 0.18 | 0 | 0.01 | 0.15 | 0.69 | 9.07 |
| 5 | | | 48 | 0.23 | 0 | 0 | 0.10 | 0.76 | 12.74 |
| 5 | | | 72 | 0.29 | 0 | 0 | 0.05 | 0.79 | 14.14 |
| 6 | 0.20 | 0.00 | 24 | 0.22 | 0 | 0 | 0.12 | 0.42 | 5.64 |
| 6 | | | 48 | 0.27 | 0 | 0 | 0.08 | 0.43 | 8.86 |
| 6 | | | 72 | 0.32 | 0 | 0 | 0.03 | 0.46 | 11.33 |
| 7 | 0.20 | 0.20 | 24 | 0.23 | 0 | 0 | 0.15 | 0.54 | 7.29 |
| 7 | | | 48 | 0.25 | 0 | 0 | 0.13 | 0.53 | 11.15 |
| 7 | | | 72 | 0.22 | 0 | 0 | 0.07 | 0.66 | 13.09 |
| 8 | 0.20 | 0.40 | 24 | 0.21 | 0 | 0 | 0.15 | 0.62 | 8.46 |
| 8 | | | 48 | 0.25 | 0 | 0 | 0.13 | 0.70 | 12.38 |
| 8 | | | 72 | 0.27 | 0 | 0 | 0.06 | 0.53 | 13.65 |
| 9 | 0.20 | 0.60 | 24 | 0.25 | 0 | 0 | 0.14 | 0.63 | 9.43 |
| 9 | | | 48 | 0.21 | 0 | 0 | 0.08 | 0.72 | 13.15 |
| 9 | | | 72 | 0.29 | 0 | 0 | 0.03 | 0.73 | 14.40 |
| 10 | 0.20 | 1.00 | 24 | 0.24 | 0 | 0.02 | 0.14 | 0.75 | 10.32 |
| 10 | | | 48 | 0.25 | 0 | 0 | 0.08 | 0.78 | 14.12 |
| 10 | | | 72 | 0.31 | 0 | 0.01 | 0.04 | 0.80 | 14.31 |
| 11 | 0.40 | 0.00 | 24 | 0.26 | 0 | 0 | 0.16 | 0.56 | 8.00 |
| 11 | | | 48 | 0.31 | 0 | 0 | 0.10 | 0.64 | 12.04 |
| 11 | | | 72 | 0.27 | 0 | 0 | 0.04 | 0.67 | 13.77 |
| 12 | 0.40 | 0.20 | 24 | 0.22 | 0 | 0 | 0.14 | 0.62 | 9.24 |
| 12 | | | 48 | 0.29 | 0 | 0 | 0.09 | 0.69 | 13.55 |
| 12 | | | 72 | 0.28 | 0 | 0 | 0.03 | 0.70 | 14.01 |
| 13 | 0.40 | 0.40 | 24 | 0.25 | 0 | 0 | 0.15 | 0.69 | 10.15 |
| 13 | | | 48 | 0.29 | 0 | 0 | 0.09 | 0.75 | 13.64 |
| 13 | | | 72 | 0.33 | 0 | 0 | 0.05 | 0.77 | 14.40 |
| 14 | 0.40 | 0.60 | 24 | 0.24 | 0 | 0.02 | 0.14 | 0.73 | 10.89 |
| 14 | | | 48 | 0.31 | 0 | 0 | 0.09 | 0.79 | 13.84 |
| 14 | | | 72 | 0.34 | 0 | 0 | 0.04 | 0.78 | 14.19 |
| 15 | 0.40 | 1.00 | 24 | 0.26 | 0 | 0.02 | 0.13 | 0.76 | 11.35 |
| 15 | | | 48 | 0.32 | 0 | 0 | 0.08 | 0.82 | 14.30 |
| 15 | | | 72 | 0.29 | 0 | 0 | 0.05 | 0.83 | 14.54 |

At each level of M1 tested the addition of DISTILLASE® improved the fermentation rate and yield of ethanol, as shown in FIG. 3, Panels A, B and C.

The starch analyses of the DDGS are shown in Table 4. From these analyses and the amount of DDGS, an estimate was then made of the amount of starch that remained unconverted in the fermenter. As indicated by these results, the addition of DISTILLASE® to M1 helps improve the hydrolysis of uncooked starch.

TABLE 4

| Trial | M1 GAU/g | Dist. GAU/g | % V/V Ethanol | DDGS gm DS | % Starch | % Unused Starch |
|---|---|---|---|---|---|---|
| 1 | 0.10 | 0.00 | 6.95 | 13.93 | 52.37 | 46.75 |
| 2 | 0.10 | 0.20 | 11.44 | 8.88 | 26.84 | 15.29 |
| 3 | 0.10 | 0.40 | 12.98 | 7.29 | 15.60 | 7.29 |
| 4 | 0.10 | 0.60 | 13.63 | 6.74 | 9.53 | 4.12 |
| 5 | 0.10 | 1.00 | 14.14 | 6.68 | 5.60 | 2.40 |
| 6 | 0.20 | 0.00 | 11.33 | 9.51 | 33.64 | 20.51 |
| 7 | 0.20 | 0.20 | 13.09 | 7.53 | 16.84 | 8.13 |
| 8 | 0.20 | 0.40 | 13.65 | 6.72 | 8.88 | 3.83 |
| 9 | 0.20 | 0.60 | 14.40 | 6.37 | 3.75 | 1.53 |
| 10 | 0.20 | 1.00 | 14.31 | 6.36 | 2.50 | 1.02 |
| 11 | 0.40 | 0.00 | 13.77 | 7.00 | 9.43 | 4.23 |
| 12 | 0.40 | 0.20 | 14.01 | 6.78 | 8.57 | 3.73 |
| 13 | 0.40 | 0.40 | 14.40 | 6.38 | 3.12 | 1.28 |
| 14 | 0.40 | 0.60 | 14.19 | 6.44 | 2.02 | 0.83 |
| 15 | 0.40 | 1.00 | 14.54 | 6.41 | 1.61 | 0.66 |

Thus, the results obtained in these Examples indicate that adding a glucoamylase preparation with a GSH ratio greater than 1.5 to a glucoamylase with GSH ratio less than 0.6 can hydrolyze uncooked starch such that ethanol fermentations can be carried out on mashes that are not cooked. These results demonstrated the percent composition of a high GSH ratio glucoamylase to a low GSH ratio as low as 9% is very effective in hydrolysing uncooked starch.

Example 4

Influence of Stillage on the Fermentation of Cooked and Non-Cooked Mash

This Example describes experiments designed to evaluate the fermentation of liquefied corn mash containing various levels of stillage compared to the fermentation of non-cooked corn mash containing various levels of stillage. The enzymes used in the fermentations were different. FERMENZYME® was used for fermenting the liquefied mash, which is a preparation that is similar to what is used commercially. For the non-cooked mash fermentation, a combination of DISTILLASE® and the RSH enzyme M1 were used.

The experiment was set up so that the corn solids would be constant while the solids from the stillage would vary. This meant that the total solids in the fermenters increased as the stillage increased. Thin stillage was obtained from a local dry mill ethanol plant. The thin stillage was concentrated in a vacuum rotary evaporator to 44% solids. It was necessary to concentrate the thin stillage, so that the total solids in the fermenters would be manageable mash composition for each fermenter is shown in Table 5.

TABLE 5

| | Fermenter Mash Composition | | | |
|---|---|---|---|---|
| | 31% Liquefied Corn at pH 5.0, .25 gm yeast, 150 gm Total .4 GAU/gm Fermenzyme | | | |
| No | Liquefact gm | Stillage Syrup gm | Water gm | Mash % DS |
| 1 | 130 | 0 | 20.0 | 31.1 |
| 2 | 130 | 2 | 18.0 | 31.7 |
| 3 | 130 | 5 | 15.0 | 32.5 |
| 4 | 130 | 10 | 10.0 | 34.0 |
| 5 | 130 | 15 | 5.0 | 35.5 |
| 6 | 130 | 20 | 0.0 | 36.9 |
| | 31% Noncooked Corn <30 mesh at pH 5.0, .25 gm Yeast, 150 gm Total .6 GAU/gm Distillase + .19 RHU/gmM1 + GC106 equivalent | | | |
| No | Corn gm | Stillage Syrup gm | Water gm | Mash % DS |
| 7 | 52.4 | 0 | 97.1 | 30.9 |
| 8 | 52.4 | 2 | 95.1 | 31.5 |
| 9 | 52.4 | 5 | 92.1 | 32.4 |
| 10 | 52.4 | 10 | 87.1 | 33.9 |
| 11 | 52.4 | 15 | 82.1 | 35.3 |
| 12 | 52.4 | 20 | 77.1 | 36.8 |
| 13 | 52.4 | 25 | 72.1 | 38.3 |
| 14 | 52.4 | 30 | 67.1 | 39.7 |

The enzyme used for the liquefied corn mash was 0.4 GAU/gm of corn liquefact of FERMENZYME®. FERMENZYME®, a special blend of DISTILLASE® and a fungal protease for fermenting corn mash, is commercially available from Genencor®. For the non-cooked fermentations, a combination of DISTILLASE® and M1 were used along with the equivalent amount of protease that was in the FERMENZYME® used in the liquefied corn mash test runs. As indicated in Table 5, the solids in the fermenters varied (mash % DS). The results of the fermentations are given in Table 6, below.

TABLE 6

| | | | | | | | | | | |
|---|---|---|---|---|---|---|---|---|---|---|
| | | | | HPLC Profile During Fermentation | | | | | | |
| Ferm | Mash | Stillage gm | Enzyme | Hours | % W/V DP > 2 | % W/V DP – 2 | % W/V DP – 1 | % W/V Lactic | % W/V Glycerol | % V/V Ethanol |
| 1 | Liq | 0 | Fermenzyme | 24 | 4.93 | 3.63 | 1.66 | 0.69 | 0.60 | 8.74 |
| 1 | | | | 48 | 1.50 | 0.56 | 2.17 | 0.88 | 0.83 | 14.08 |
| 1 | | | | 72 | 0.71 | 0.56 | 0.17 | 0.84 | 0.85 | 16.28 |
| 2 | Liq | 2 | Fermenzyme | 24 | 5.34 | 3.94 | 1.72 | 0.82 | 0.79 | 9.33 |
| 2 | | | | 48 | 1.77 | 0.61 | 4.06 | 0.99 | 1.03 | 12.85 |
| 2 | | | | 72 | 0.90 | 0.61 | 3.14 | 0.99 | 1.04 | 14.04 |
| 3 | Liq | 5 | Fermenzyme | 24 | 5.75 | 4.40 | 1.80 | 0.98 | 1.07 | 9.35 |
| 3 | | | | 48 | 2.07 | 0.65 | 4.66 | 1.13 | 1.27 | 11.92 |
| 3 | | | | 72 | 1.14 | 0.68 | 3.26 | 1.16 | 1.35 | 13.54 |
| 4 | Liq | 10 | Fermenzyme | 24 | 5.74 | 4.31 | 1.55 | 1.15 | 1.28 | 9.41 |
| 4 | | | | 48 | 2.28 | 0.72 | 5.21 | 1.36 | 1.56 | 11.80 |
| 4 | | | | 72 | 1.35 | 0.75 | 4.73 | 1.36 | 1.59 | 12.88 |
| 5 | Liq | 15 | Fermenzyme | 24 | 6.26 | 4.65 | 1.64 | 1.47 | 1.56 | 9.66 |
| 5 | | | | 48 | 2.56 | 0.87 | 5.50 | 1.59 | 1.82 | 11.56 |
| 5 | | | | 72 | 1.57 | 0.84 | 4.71 | 1.58 | 1.83 | 12.58 |
| 6 | Liq | 20 | Fermenzyme | 24 | 6.16 | 1.67 | 1.67 | 1.64 | 1.81 | 9.30 |
| 6 | | | | 48 | 2.75 | 0.91 | 5.79 | 1.77 | 2.05 | 11.57 |
| 6 | | | | 72 | 1.83 | 1.00 | 6.48 | 1.82 | 2.00 | 11.63 |
| 7 | g. corn | 0 | Distillase + M1 + GC106 | 24 | 0.34 | 0 | 0.01 | 0.14 | 0.67 | 11.86 |
| 7 | | | | 48 | 0.36 | 0 | 0 | 0.17 | 0.78 | 15.65 |
| 7 | | | | 72 | 0.39 | 0 | 0 | 0.18 | 0.86 | 17.48 |
| 8 | g. corn | 2 | Distillase + M1 + GC107 | 24 | 0.35 | 0 | 0.02 | 0.23 | 0.77 | 11.96 |
| 8 | | | | 48 | 0.40 | 0 | 0 | 0.25 | 0.88 | 16.09 |
| 8 | | | | 72 | 0.38 | 0 | 0 | 0.19 | 0.95 | 17.56 |
| 9 | g. corn | 5 | Distillase + M1 + GC108 | 24 | 0.40 | 0 | 0.02 | 0.38 | 0.88 | 12.07 |
| 9 | | | | 48 | 0.42 | 0 | 0 | 0.38 | 0.99 | 15.99 |
| 9 | | | | 72 | 0.43 | 0 | 0 | 0.31 | 1.07 | 18.03 |
| 10 | g. corn | 10 | Distillase + M1 + GC109 | 24 | 0.54 | 0 | 0.03 | 0.65 | 1.02 | 11.31 |
| 10 | | | | 48 | 0.53 | 0 | 0 | 0.66 | 1.18 | 15.95 |
| 10 | | | | 72 | 0.52 | 0 | 0 | 0.65 | 1.24 | 17.69 |
| 11 | g. corn | 15 | Distillase + M1 + GC110 | 24 | 0.70 | 0 | 0 | 0.83 | 1.18 | 10.22 |
| 11 | | | | 48 | 0.66 | 0 | 0.10 | 0.87 | 1.40 | 15.53 |
| 11 | | | | 72 | 0.62 | 0 | 0 | 0.83 | 1.42 | 17.14 |
| 12 | g. corn | 20 | Distillase + M1 + GC111 | 24 | 0.82 | 0 | 0 | 1.15 | 1.47 | 10.04 |
| 12 | | | | 48 | 0.78 | 0 | 0 | 1.09 | 1.52 | 14.32 |
| 12 | | | | 72 | 0.78 | 0 | 0 | 1.04 | 1.70 | 17.24 |
| 13 | g. corn | 25 | Distillase + M1 + GC112 | 24 | 1.04 | 0 | 0 | 1.48 | 1.78 | 7.71 |
| 13 | | | | 48 | 1.01 | 0 | 0 | 1.40 | 1.77 | 11.40 |
| 13 | | | | 72 | 0.99 | 0 | 0 | 1.42 | 1.97 | 14.72 |
| 14 | g. corn | 30 | Distillase + M1 + GC113 | 24 | 1.17 | 0 | 0 | 1.74 | 2.02 | 7.68 |
| 14 | | | | 48 | 1.18 | 0 | 0 | 1.70 | 2.06 | 11.61 |
| 14 | | | | 72 | 1.12 | 0 | 0 | 1.65 | 2.18 | 14.58 |

In commercial practice, a certain amount of the stillage is recycled for the yeast nutrient content and to help the water balance in the plant. Thus, fermentation systems that are less influenced by stillage is very desirable in industrial fermentation plants. The results of these experiments show that stillage effects the fermentation of liquefied mash more than in non-cooked mash.

FIG. 4 shows the response of ethanol to the amount of stillage added in both types of mashes. In both cases, increasing the stillage solids reduced the ethanol level. But as FIG. 4 shows, the non-cooked mash is much less sensitive to stillage than the cooked mash.

FIG. 5 shows the glucose profile after 72 hour of fermentation and the results are very striking. As the stillage solids increased in cooked mash more glucose was left unfermented, while in the non-cooked mash, essentially non-detectable levels of glucose were observed at all levels of stillage. This observation is very significant because as the starch was hydrolyzed it was immediately to ethanol by the yeast. This level of glucose build-up is very unusual. This observation is also important particularly with respect to the yeast, in that even though the glucose level is extremely low, the yeast remain very active in fermenting. In contrast, in the cooked mash, even when glucose was in ample supply, the yeast could not ferment the glucose.

FIG. 6 is a plot of the disaccharides after 72 hours of fermentation with respect to stillage added. The disaccharide levels for the non-cooked mash were found to be essentially non-detectable throughout the range of stillage added, but in the cooked mash as the stillage level increased the disaccharides increased.

As indicated in FIG. 7, the higher sugars (i.e., oligosaccharides greater than disaccharides) provided a somewhat a similar picture, as the level of higher sugars for the cooked mash were higher with respect to stillage added than for the non-cooked mash.

FIG. 8 shows the lactic acid level after 72 hours of fermentation. As indicated, the levels are higher for the cooked mash than the non-cooked mash. One consideration with lactic acid is that it is a measure of contamination. Although it is not intended that the present invention be limited to any particular theory or mechanism, it is possible that since both the glucose and disaccharide levels are always very low in the non-cooked mash, contaminating microorganisms have very little substrate to utilize.

FIG. 9 provides a summary of the glycerol levels after 72 hour of fermentation. As indicated, again the levels are lower at the respective stillage addition levels with the non-cooked mash than with the cooked mash. A contributing factor for glycerol formation during fermentation with yeast is the stress the yeast is under. Generally, the more stress the yeast is under, the more glycerol that will be formed. The results in FIG. 9 would indicate that at similar stillage levels, the yeast in the non-cooked mash are under less stress. But even at higher stillage levels that could be run with cooked mash, higher levels of glycerol were formed. Even with the higher glycerol level in the non-cooked mash, the yeast produced more ethanol. Thus, it appears that yeast seem to ferment more efficiently in the non-cooked mash than in the cooked mash.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

What is claimed is:

1. A method for producing ethanol as an end-product comprising the steps of:
   a) contacting a substrate comprising a ground corn slurry comprising uncooked starch with a substrate-converting enzyme and an intermediate-converting enzyme to produce an intermediate comprising glucose, wherein the substrate-converting enzyme and the intermediate-converting enzyme are both obtained from a microorganism of the genus *Rhizopus* and at least the substrate-converting enzyme is a raw starch hydrolyzing enzyme; and
   b) contacting the intermediate with an ethanologenic microorganism to produce ethanol, wherein at least 90% of the uncooked starch of the ground corn slurry is converted to the intermediate comprising glucose within 72 hours; and the glucose is converted to ethanol at a rate sufficient to maintain the concentration of the glucose at less than 0.25% by weight volume.

2. The method according to claim 1, wherein the substrate is sequentially contacted with the substrate-converting enzyme and then with the intermediate-converting enzyme.

3. The method according to claim 1, wherein the contacting step b) is conducted at a temperature of 25 to 35° C.

4. The method according to claim 1, wherein 72 hours after contacting the intermediate with the ethanologenic microorganism, the amount of ethanol produced is at least 14% after 72 hours.

5. The method according to claim 1, wherein the raw starch hydrolyzing enzyme comprises a glucoamylase which is added in the range of 0.05 to 10.0 glucoamylase units (GAU)/g of starch.

6. The method according to claim 1, wherein the ground corn slurry has a percentage of starch between about 10% and about 35%.

7. The method according to claim 1, wherein the raw starch hydrolyzing enzyme is secreted by a microorganism of the genus *Rhizopus* in contact with said uncooked starch.

8. The method according to claim 1, wherein the raw starch hydrolyzing enzyme is obtained from *R. niveus*.

9. The method according to claim 1, further comprising adding a glucoamylase derived from a microorganism of the genus *Aspergillus* to the contacting step a).

10. The method according to claim 1, further comprising adding an alpha amylase to the contacting step a).

11. The method according to claim 1, wherein the intermediate-converting enzyme is secreted by a microorganism of the genus *Rhizopus* in contact with said intermediate.

12. The method according to claim 1, wherein at least 95% of the uncooked starch is converted to the intermediate comprising glucose within 72 hours.

* * * * *